United States Patent [19]

Venable

[11] Patent Number: 4,711,580

[45] Date of Patent: Dec. 8, 1987

[54] MODELING PROPERTIES OF FLAKE FINISHES USING DIRECTIONAL RESOLUTION AND STATISTICAL FLAKE ORIENTATION DISTRIBUTION FUNCTION

[75] Inventor: William H. Venable, Falls Church, Va.

[73] Assignee: Hunter Associates Laboratory, Inc., Reston, Va.

[21] Appl. No.: 695,594

[22] Filed: Jan. 28, 1985

[51] Int. Cl.$^4$ ............... G01J 3/50; G01J 3/51; G01N 21/27; G06F 15/46

[52] U.S. Cl. ............... 356/406; 356/402; 356/446; 364/526

[58] Field of Search ............... 356/445–448, 356/244, 319, 402, 405, 406; 364/526

[56] References Cited

U.S. PATENT DOCUMENTS

| | | | |
|---|---|---|---|
| 3,060,790 | 10/1962 | Ward | 356/405 |
| 3,389,265 | 6/1968 | Schreckendgust | 356/405 |
| 3,601,589 | 8/1971 | McCarty | 364/526 X |
| 3,690,771 | 12/1972 | Armstrong, Jr. et al. | 356/405 X |
| 3,708,233 | 1/1973 | Van Dyk et al. | 356/244 |
| 3,712,745 | 1/1973 | Armstrong, Jr. et al. | 356/244 |
| 3,806,256 | 4/1974 | Ishak | 250/222 X |
| 3,814,932 | 6/1974 | Anati et al. | 250/226 |
| 3,916,168 | 10/1975 | McCarty et al. | 356/405 X |
| 3,935,436 | 1/1976 | Holschlag et al. | 364/526 X |
| 4,090,243 | 5/1978 | Kotera et al. | 364/526 |
| 4,165,180 | 8/1979 | Failes | 356/310 |
| 4,191,940 | 3/1980 | Polcyn et al. | 340/146.3 B |
| 4,278,538 | 6/1981 | Lawrence et al. | 209/580 |
| 4,344,709 | 8/1982 | Provder et al. | 356/445 |
| 4,402,611 | 6/1983 | Yuasa | 356/405 |
| 4,479,718 | 10/1984 | Alman | 356/405 |
| 4,572,672 | 2/1986 | Orchard et al. | 356/446 |

FOREIGN PATENT DOCUMENTS

0079517  5/1983  European Pat. Off. ............ 356/402

Primary Examiner—Vincent P. McGraw
Attorney, Agent, or Firm—Nixon & Vanderhye

[57] ABSTRACT

The light reflectance of metallic flake finishes can be successfully separated into a flake component and a diffuse component. An empirical model accurately represents the statistical distribution of flake orientation in extreme cases and in areas of transition between the extreme cases. Colorimetric measurements at three angles of observation are both necessary and sufficient to characterize a flake finish to the precision required in normal quality control applications. Filter colorimetry or spectrophotometry can be used to obtain the data from which the model parameters are calculated. The model parameters provide objective qualitative data describing the optical and physical characteristics of flake finishes. The parameters of the empirical model as calculated from colorimetric measurements at the three angles can be correlated with physical properties of flake finishes to facilitate matching of finishes and to provide specific guidance to operators applying finishes as to what might be changed to achieve a better match.

32 Claims, 15 Drawing Figures

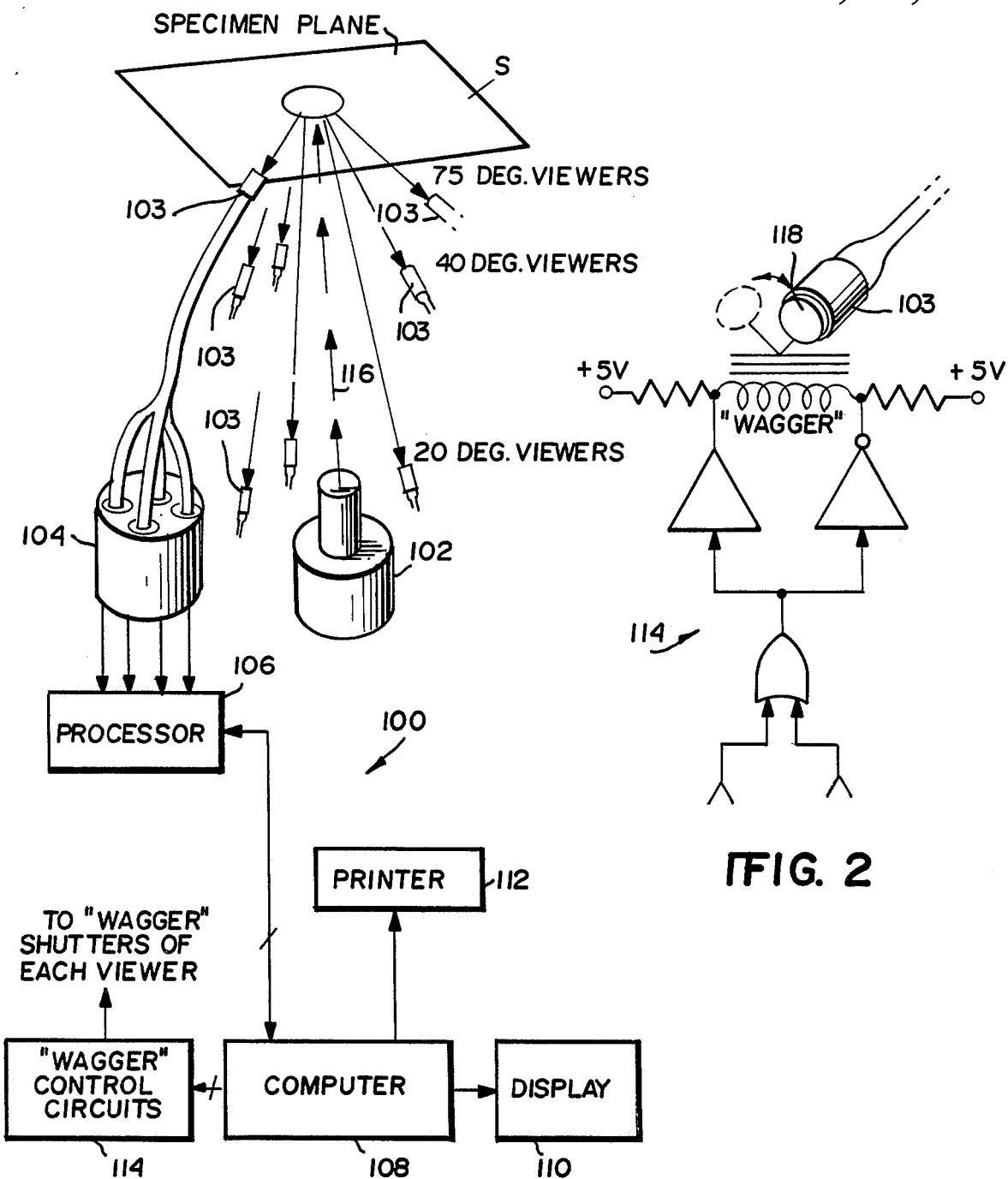

FLAKE COMPONENT

DIFFUSE COMPONENT

MODELING PROPERTIES OF FLAKE FINISHES USING DIRECTIONAL RESOLUTION AND STATISTICAL FLAKE ORIENTATION DISTRIBUTION FUNCTION

FIELD OF THE INVENTION

The present invention relates to optical analysis of finished surfaces, and more particularly, to the determination of the characteristics of metallic flake paint finishes.

BACKGROUND OF THE INVENTION

Flake finishes (finishes having a general background of high-gloss paint embedded in which are nearly-flat reflecting flakes) are commonly used (for example, in the automotive industry) for their aesthetic effect. The appearance of a flake finish changes dramatically with a change of viewpoint because of the highly directional reflective characteristics of the embedded flakes—the finish appears to "glitter" and sparkle as the eye catches the reflections of different flakes. Unfortunately, no objective qualitative analysis technique has been available in the past which is capable of accurately measuring the optical characteristics of a flake finish and relating the measurement results to the physical characteristics of the finish. The highly prized optical characteristics of flake finishes have thus made flake finish quality control, finish matching and the like extremely difficult tasks requiring skill, guesswork and much experience.

The following documents disclose various techniques for characterizing the optical properties of flake finishes:

| | |
|---|---|
| Alman | U.S. Pat. No. 4,479,718 |
| McCarty | U.S. Pat. No. 3,601,589 |
| McCarty et al | U.S. Pat. No. 3,916,168 |
| Armstrong. Jr., et al | U.S. Pat. No. 3,690,771 |
| Ward | U.S. Pat. No. 3,060,790 |
| Schreckendgust | U.S. Pat. No. 3,389,265 |
| Ishak | U.S. Pat. No. 3,806,256 |
| Anati et al | U.S. Pat. No. 3,814,932 |
| Holschlag et al | U.S. Pat. No. 3,935,436 |
| Kotera et al | U.S. Pat. No. 4,090,243 |
| Failes | U.S. Pat. No. 4,165,180 |
| Polcyn et al | U.S. Pat. No. 4,191,940 |
| Lawrence et al | U.S. Pat. No. 4,278,538 |
| Yuasa | U.S. Pat. No. 4,402,611 |
| Orchard | U.S. Pat. No. 4,572,672 |
| Van Dyk et al | U.S. Pat. No. 3,708,233 |
| Armstrong, Jr. et al | U.S. Pat. No. 3,712,745 |
| Provder et al | U.S. Pat. No. 4,344,709 |
| European Patent Publication No. 0 079 517 | |

U.S. Pat. No. 4,479,718 to Alman (1984) teaches based on empirical data that colorimetric measurements at three angles (110°, 45° and 15° from the direction of a specular beam) are necessary and sufficient to characterize the optical properties of a flake finish. See also U.S. Pat. No. 4,572,672 to Orchard (1986). Thus, the prior art teaches performing colorimetric measurements of light reflected by a flake finish at three different angles to permit matching of different finishes.

Unfortunately, tri-stimulus (Lab) values produced by goniometric analysis have only limited usefulness in matching paint finishes, for they provide little guidance as to what steps might be taken to make mismatched flake finishes match better.

Tri-stimulus values indicate the color appearance and, more importantly to most applications, the magnitude and direction of the difference in color appearance between a standard finish and a finish under measurement. Although differences in tri-stimulus values obtained from measurement of different flake finishes indicate the magnitude of differences in appearance of the finishes, trial and error (along with much experience and skill) is necessary to interpret tri-stimulus difference values and take appropriate corrective action.

A flake finish analysis technique which provides specific guidance concerning what physical characteristics of the finish under test should be altered to achieve closer matching with a standard finish would be extremely valuable.

SUMMARY OF THE INVENTION

The present invention provides measurements of the optical characteristics of a finish having flakes embedded therein.

In accordance with one aspect of the present invention, a radiation sensing device receives radiation reflected by a finish along first, second and third paths and converts the received radiation into corresponding first, second and third electrical input signals. A digital signal processor connected to receive the electrical input signals produces, in response to the electrical input signals, a first output signal representing the spectral content of a component of radiation diffusely reflected by the finish; a second output signal representing the spectral content of a component of radiation specularly reflected by the flakes embedded in the finish; and a third output signal representing statistical distribution of the orientation of the flakes with respect to a predetermined orientation.

By comparing the values of the first, second and third output signals measured for different finishes, mismatches in the optical characteristics of the different finishes can be ascertained. The output signals provided by the present invention correspond to parameters of a statistical model. These parameter values can be used to provide practical guidance not previously available facilitating matching of finishes, as the parameters correspond to physical characteristics of the finish, such as flake orientation, flake reflectivity and the like.

Comparison of the parameter values yielded by the present invention for optical measurement of two different finishes indicates how the finishes are mismatched and what finish characteristics can be changed to make them match better. The parameters produced by the present invention are far more useful than prior art measurement results, which provide little specific guidance as to what steps might be taken to achieve a better match between finishes.

BRIEF DESCRIPTION OF THE DRAWINGS

These and other features of the present invention will be better and more completely understood by studying the following detailed description of presently preferred embodiments together with appended drawings, of which:

FIG. 1 is a schematic block diagram of a presently preferred exemplary embodiment of a measuring and analyzing apparatus in accordance with the present invention;

FIG. 2 is a schematic diagram of the "wagger" shutter and associated control circuit used to selectively analyze reflected radiation received by the viewers shown in FIG. 1;

DETAILED DESCRIPTION OF A PREFERRED EMBODIMENT

(A) BLOCK DIAGRAM OF A FLAKE COLORIMETER

Figure 3:
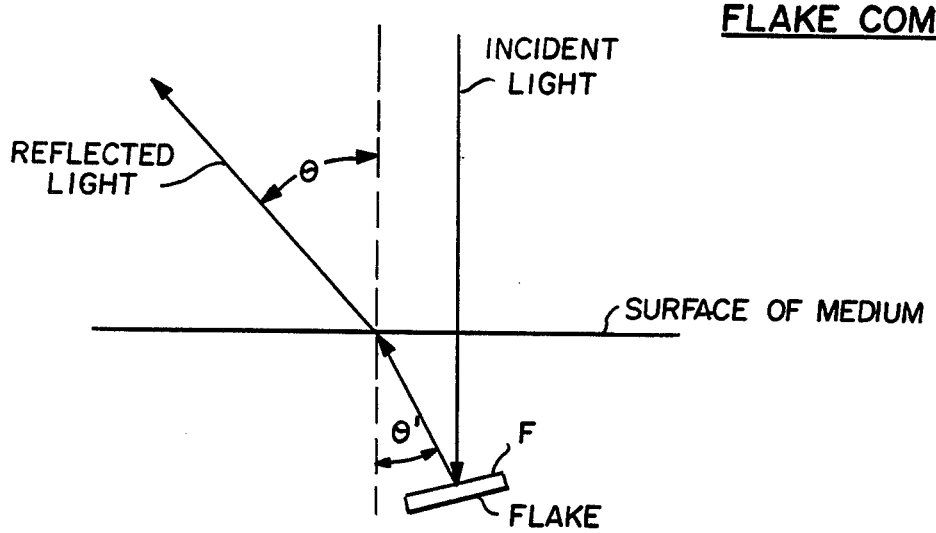
FIG. 3 is a schematic representation of an exemplary reflected beam contributing to the flake component of radiation reflected by an exemplary flake finish.

FIG. 1 is a schematic block diagram of a presently preferred exemplary embodiment of a flake colorimeter 100 in accordance with the present invention. Colorimeter 100 includes a light source 102, three or more viewers 103 (nine are used in the preferred embodiment) and associated sensor modules 104, a D-9 processor 106, a digital signal processor ("computer") 108, a display 110, a printer 112 and "wagger" control circuits 114.

Light source 102 is a standard D-25P projector (manufactured by HunterLab of Reston, Va.), which produces a beam 116 of light and may direct the beam toward the plane of a specimen S to be analyzed. Beam 116 is directed substantially normal to the specimen plane in the preferred embodiment, although other source angles could be used. Viewers 103 sense portions of beam 116 reflected by specimen S. Each of viewers 103 in the preferred embodiment includes nine optical fiber bundles, each of which is divided into four groups of fibers. The four groups of fibers are coupled to four corresponding conventional colorimetric sensors (of the filter type) of a conventional sensor module 104 (e.g., model D-25M manufactured and sold by Hunter-Lab of Reston, Va.). Light received by each of viewers 103 can be selectively blocked or passed by a "wagger" shutter similar to those used in LabScan spectrocolorimetry instruments manufactured and sold by HunterLab.

FIG. 2 is a schematic diagram of a viewer 103, a wagger 118 and an associated wagger control circuit 114. Wagger 118 mechanically moves between a first position (shown in phantom in FIG. 2) whereat its associated viewer 103 is not obstructed and can therefore receive light reflected (scattered) by specimen S; and a closed position (shown in solid lines in FIG. 2) whereat the wagger prevents its associated viewer from receiving light. Wagger control circuit 114 changes the position of wagger 118 in response to TTL logic signals received from processor 108. Each wagger 118 can be controlled individually or in groups of three in the preferred embodiment using replications of the circuitry shown in FIG. 2.

The signal produced by sensor module(s) 104 are processed with a D-9 processor 106 (manufactured and sold by HunterLab) which includes a special (conventional) operating program option allowing the D-9 to be operated by means of external processor 108. Processor 108 in the preferred embodiment is a Columbia Data Systems M48 computer. Processor 108 controls the operation of D-9 processor 106, and receives electrical input signals from the D-9 processor responsive to the colorimetry of the light received by unobstructed ones of viewers 103. Processor 108 produces an output on display 110 and/or printer 112 and also controls wagger control circuits 114.

(B) PRINCIPLES OF MEASUREMENT—A DESCRIPTIVE MODEL

The preferred embodiment of flake colorimeter 100 in accordance with the present invention measures the characteristics of what will be referred to herein as "flake finishes". Such finishes consist essentially of a general background of high-gloss paint embedded in which are a large number of nearly flat reflecting flakes. The light reflected from such a specimen is divided into three principal categories or components in accordance with a model of the present invention: a "surface component," a "flake component," and a "diffuse component."

Light reflected from the shiny first surface of a specimen is called the "surface component." This surface component is spectrally very similar to the light from the source 102, with a slight emphasis on the blue end of the spectrum. For flat specimens with smooth surfaces, the surface component is not measured by the preferred embodiment, and is not directly involved in the measurements performed by the present invention.

Light reflected directly from the surfaces of the flakes embedded in the flake finish makes up the "flake component." FIG. 3 graphically shows the path of a typicl ray of light as reflected by a flake F. After the bending of the incident light as it enters and exits the outer surface above the finish is taken into account, the path of such a ray is that of an ordinary mirror-like reflection. The preferred embodiment assumes that the surface of each flake F is flat. However, slight departures from flatness for individual flakes will not cause failure of a specimen to conform with the descriptive model of the present invention is any significant way.

Figure 4:
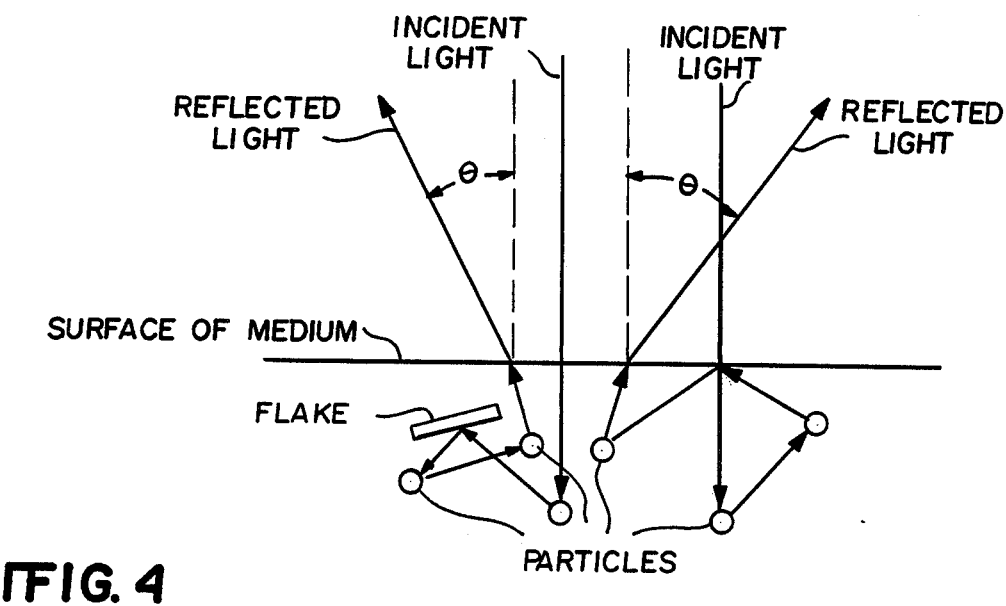
FIG. 4 is a schematic representation of two exemplary reflected beams contributing to the diffuse component of radiation reflected by an exemplary flake finish.

Light diffusely reflected by scattering is referred to as the "diffuse component." The diffuse component includes what is left over after the first two components (the surface component and the flake component) are taken into consideration. The diffuse component primarily comprises components of light which emerge after many encounters with pigment particles and, occasionally, with embedded flakes as well. FIG. 4 is a graphical illustration of two representative paths of beams of light diffusely reflected by scattering.

Flake colorimeter 100 of the present invention models the optical characteristics of a specimen using a mathematical, statistical description of the combined flake and diffuse components of radiation specularly and diffusely reflected, respectively, by specimen S.

As mentioned previously, light source 102 directs a beam of radiation perpendicular to the surface of specimen S. For purposes of the discussion presented herein, specimen S is assumed to be flat and non-directional (in the sense that there is no preference for reflecting to the left, the right, fore or aft). Departures from flatness and non-directionality will be discussed briefly later on.

Under these conditions, the reflectance factor, R, of the specimen S will be a function only of the polar angle $\theta$, that is, the angle between a given direction and the direction perpendicular to the surface of the specimen. In the model of the present invention, $R(\theta)$ will be considered to be the product of a first function, $E(\theta)$, and the sum of two additional functions, $D(\theta')$ and $F(\theta')$, or, in the form of a mathematical equation:

$$R(\theta) = E(\theta) * [D(\theta') + F(\theta')]. \quad (1)$$

Figure 5:
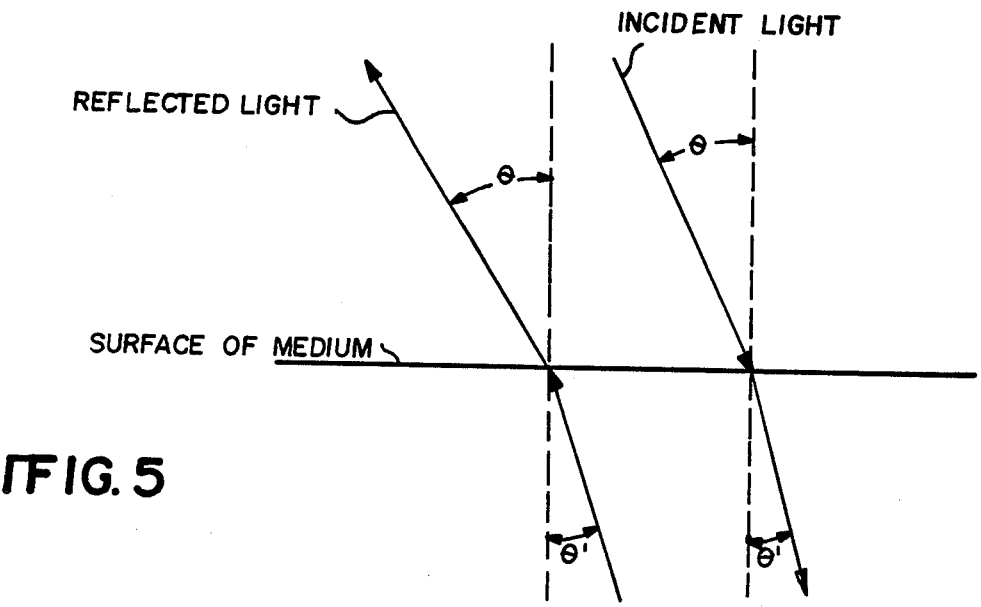
FIG. 5 is a graphical illustration of the relationship between interior polar angles $\theta'$ and exterior polar angles $\theta$ for radiation incident to and reflected by a flake finish.

In equation 1, $\theta$ represents angle as measured outside the smooth surface of specimen S, and $\theta'$ is the corresponding angle, as given by the laws of optical refraction, inside the specimen surface. $\theta$ will be referred to herein as the exterior polar angle and $\theta'$ as the interior polar angle. Exemplary angles $\theta$ and $\theta'$ are graphically illustrated in FIG. 5 for incident and reflected beams.

The nature and meaning of each of the four functions expressed in the equation (1) will now be discussed in the order of their appearance in the equation.

The reflectance factor $R(\theta)$ is the ratio of the measure, obtained by some process, of the radiation emerging from the specimen S at exterior angle $\theta$ to the measure which would be obtained by the same process if the specimen were a perfect diffuse reflector. By definition, a perfect diffuse reflector is a specimen which reflects all of the radiation striking it and with no preferred direction. In the preferred embodiment, reflectance factor is expressed in terms of a percentage. Thus, $R(\theta)$ for a perfect diffuse deflector, by definition, is a constant 100% no matter how it is measured. Equation (1) describes how the distribution of reflected radiation from a flake finish specimen compares to the distribution of reflected radiation from perfect diffuse reflector.

Figure 6:
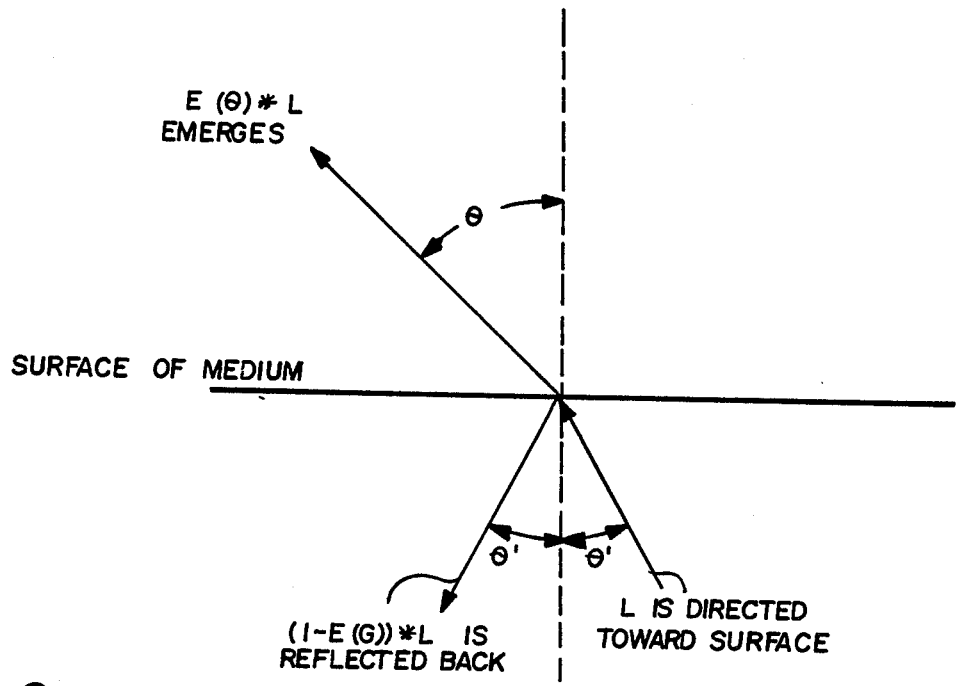
FIG. 6 is a graphical illustration of the physical significance of the emissivity function $E(\theta)$ of the model in accordance with the present invention.
Figure 7:
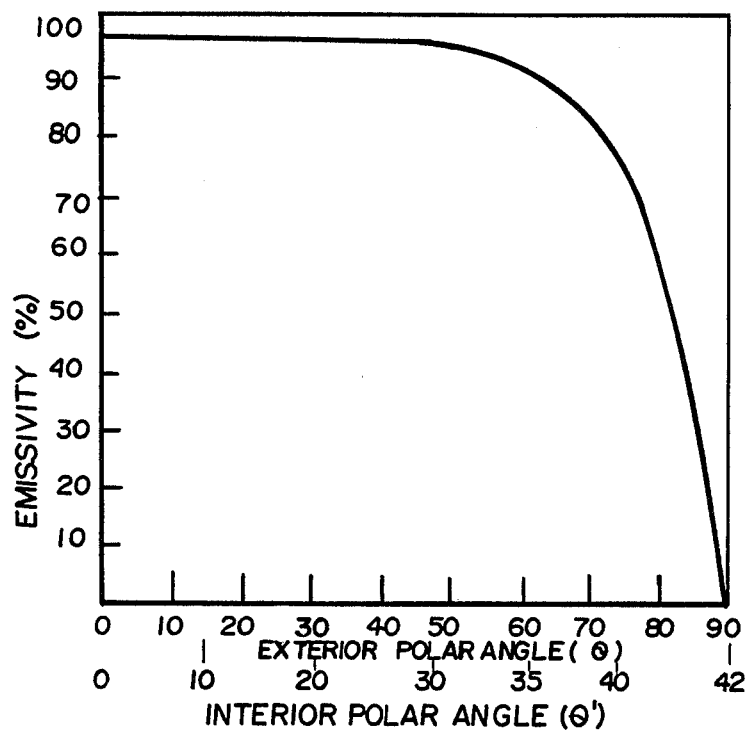
FIG. 7 is a plot of the emissivity function $E(\theta)$ with respect to polar angle.

The function $E(\theta)$ is termed "emissivity" herein. As light within the specimen S and directed toward the outside of the specimen strikes the smooth interface between the specimen and the surrounding air, a portion of the light is reflected back into the specimen. The rest of the light emerges to the outside where it can be measured by flake colorimeter 100. $E(\theta)$ is that fraction of the radiation which emerges, given as a function of the direction in which the radiation emerges. FIG. 6 is a graphical illustration of emissivity in terms of a beam of light emerging at a particular exemplary angle $\theta$. FIG. 7 graphically illustrates how $E(\theta)$ varies with interior and exterior polar angle. The preferred embodiment assumes an index of refraction of 1.5 for specimen S.

The function $D(\theta')$ in equation (1) expresses the distribution of the light in the diffuse component. Before the light in the diffuse component is modified by passing through the surface of the finish, this light is distributed with respect to angle in the same way as is light reflected from a perfect diffuser—that is to say, $D(\theta')$ is a constant. Because some light is absorbed in any real specimen, $D(\theta')$ will always be less than $100 * E(0°)$, and usually considerably less.

A factor $E(0°)$ is included in expressing the upper limit for $D(\theta')$ in order to take into account that some of the incident light (the surface component) is reflected from the surface on the way into the specimen and never has a chance to be diffusely reflected. However, the preferred embodiment performs calculations in terms of measured emerging light so that the initial loss of light upon entering the specimen is automatically taken into account.

Figure 8:
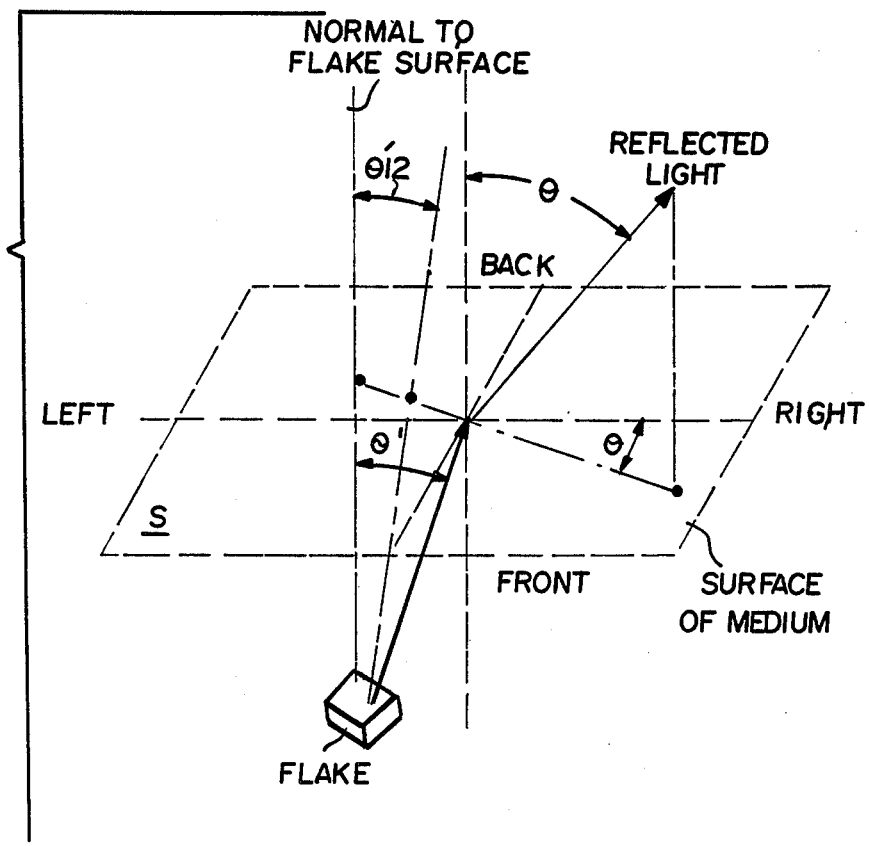
FIG. 8 is a geometric representation of flake reflection showing exterior polar angle $\theta$, interior polar angle $\theta'$, flake orientation angle $\theta'/2$ and azimuth angle $\phi$ for an arbitrary origin.

The function $F(\theta')$ of equation (1) describes the distribution of the flake component with respect to internal polar angle. This function $F(\theta')$ is somewhat more complex than the function $D(\theta')$ discussed above. Because flakes are fairly large and flat, they tend to settle into positions whereat the plane of the flake surface is very nearly parallel the plane of the surface of the finish. FIG. 8 schematically illustrates the angles used to describe flake orientation in the present invention.

Since the person applying the finish has no control over the individual flakes, it is impossible to predict the orientation of any one flake. However, this very lack of control allows one to predict the general behavior of a large number of flakes using statistical principles. In the present invention, $F(\theta')$ is an approximate probability function which represents a compromise between being reasonably simple to calculate and representing the expected distribution of reflected light accurately.

The statistical basis and the associated approximations for the set of functions used to describe the flake component in accordance with the present invention will now be presented. This function $F(\theta')$ is derived in terms of a fairly rigorous treatment of two extreme cases. In one extreme case, the flakes embedded in the finish of specimen S are tightly bound to being flat. In the other extreme case, such flakes are completely free. Function $F(\theta')$ in the preferred embodiment also includes an empirical function used to describe the transition between the two extreme cases.

If the flakes are large and tend to be forced very strongly to lie parallel to the surface of the finish, the flakes tend to have a normal distribution centered about the orientation parallel to the finish surface. Under such conditions of tight binding of the flakes, the function $F(\theta')$ describing the distribution of the reflected light has the form FBOUND $(\theta')$ given by the following expression:

$$FBOUND(\theta') = \frac{\cos(\theta'/2) * e^{ln(\frac{1}{2}) * (\theta'/W)^2}}{\sin \theta'} \quad (2)$$

The form of equation 2 is based primarily on the assumption that if the forces tending to orient the flakes parallel to the medium surface are strong, the distribution of flakes will be a statistical normal distribution with respect to the polar angle $\theta'$ centered about 0°, with the flakes being free, and therefore uniformly distributed with respect to azimuth. Since the total solid angle available per unit range of polar angle varies as the sine of the polar angle, the density of radiation per unit solid angle is proportional to the error function divided by the sine of the polar angle, where the error function is expressed as follows:

$$e^{ln\frac{1}{2}*(\theta'/W)^2}. \quad (3)$$

The multiplying factor $\cos(\theta'/2)$ appears in equation 2 because as a flake becomes more tilted, it intercepts less of the perpendicularly incident light. The factor 2 dividing the angle $\theta'$ is included because $\theta'$ represents the angle of reflection of the radiation, whereas the amount of radiation intercepted varies as the cosine of the polar angle of tilt of the flake itself.

In the other extreme case, where the flakes are completely free to orient themselves in any direction, the density of outgoing radiation is given simply by the following expression:

$$FFREE(\theta') = \cos(\theta'/2). \quad (4)$$

Since radiation escapes the finish only for $\theta'$ less than the critical angle (roughly, $\theta' = 45°$), the cosine factor in both equations 2 and 4 is never less than 0.91. Furthermore, since most of the radiation is reflected at an even smaller angle, the cosine function is never much different from one, and can be omitted both equations 2 and 4 with no great loss in fitting accuracy.

The transition from the model expressed in equation 2 to the model expressed in equation 4 is handled by making use of the fact that the limiting form of the error function (equation 3) for large values of the width W is simply a constant, so that all that is required to complete the transition is some empirical treatment of the denominator so that the sine function of equation (2) will "fade" into a constant value of unity.

In the preferred embodiment, a transition function FTRAN (W) is defined in the form of the following expression:

$$FTRAN(W) = \frac{1}{(1 + e^{(W-T1)/T2})} \quad (5)$$

The expression set forth in equation 5 is used as a weighing function to produce a transition from the sine function to a simple constant. This FTRAN function is incorporated in the denominator of equation 2 to provide a transition from the tightly bound case in which the sine function dominates the denominator to the free case in which the denominator is constant.

Equation 6 below expresses the statistical model of the flake component $F(\theta')$ in accordance with the present invention:

$$F(\theta') = \frac{\cos(\theta'/2) * e^{(ln(\frac{1}{2})*(\theta'/W)^2)}}{(FTRAN(W)*\sin(\theta')) + 1 - FTRAN(W)} \quad (6)$$

The model set forth in equation 6 above, with T1 = 22.8° and T2 = 2.62°, fits all experimental data currently available as accurately as the quality of the data will allow. As more accurate data are available, a more sophisticated model of the transition from the bound case to the free case may become apparent. However, the usefulness of this model in establishing a match between specimens produced in a similar way or in establishing in what way such specimens differ has not been found to be strongly affected by small failures in the model to predict goniophotometric curves exactly. The complexity of the flake material and the measurement uncertainties in the goniophotometric data currently available both suggest that further refinements of the model will be of more academic than practical interest.

Figure 9:
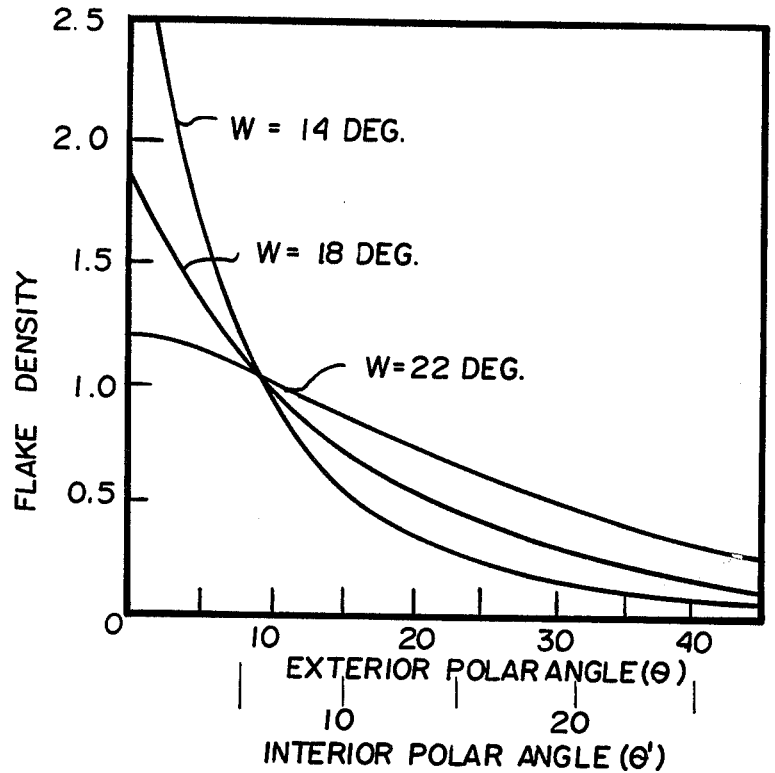
FIG. 9 is a graphical illustration of an exemplary modeled distribution of the flake component for three values of the width parameter W of the model of the present invention.

FIG. 9 illustrates several exemplary distributions of the flake component $F(\theta')$. As will be explained, two values are sufficient and necessary to completely specify the flake component. The first value, which will be called "width" (W) and will be given in degrees of angle, serves as a measure of the expected range of $\theta$ over which the flake component is reasonably large. Thus, the "width" determines which general shape will be used for the $F(\theta')$ curve. W is a measure of the range of polar angles of orientation of the flakes. When the flakes have a strong tendency to line up parallel to the surface of the finish (e.g., when flakes are large or the coating is thin), W tends to be small. When the flakes are small or the coating is thick, the flakes tend to orient themselves in a more random fashion, corresponding to a larger width value W. For flake finishes experimentally evaluated with flake colorimeter 100, W has ranged from W = 13° to W = 25°.

For the second value to characterize the flake component $F(\theta')$, a measure of the total amount (magnitude) of light reflected by the flakes is used. The preferred embodiment uses the average reflectance factor measured with uniform sensitivity in all directions. This is the quantity which would be obtained if the flake component could somehow be measured by itself, exclusive of the direct and diffuse components, with an integrating sphere instrument.

From the foregoing, it can be seen that three values, one for the diffuse component and two for the flake component, are required to predict the reflectance factor of a specimen S at all angles. This entails, in turn, three independent measurements.

Because the flake component varies strongly with direction whereas the diffuse component does not, one measurement is insufficient to allow one to predict the reflectance factor at all angles. However, as will be explained, two measurements are also insufficient.

Figure 10:
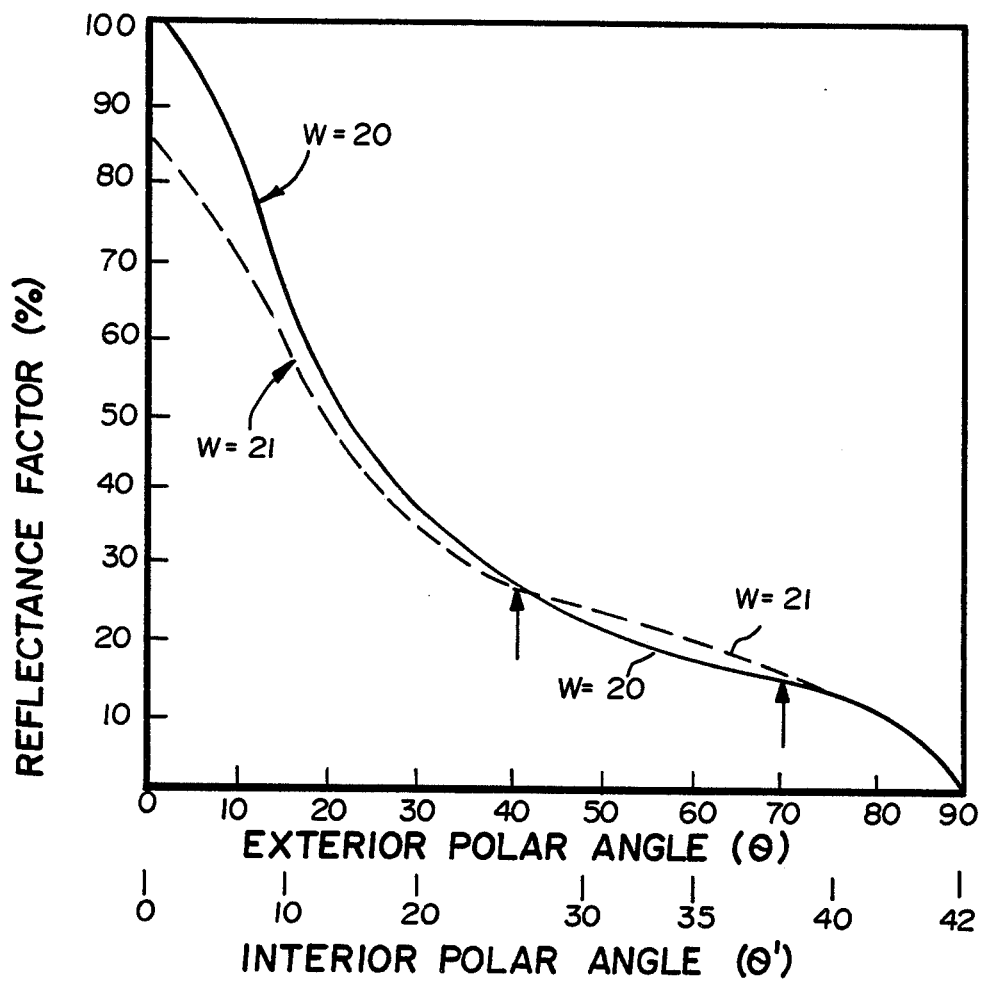
FIG. 10 is a graphical illustration of reflectance factor curves of two exemplary mismatched flake finishes.

As an illustration of a problem which could arise if only two measurements are made, consider the pair of reflectance factor curves shown in FIG. 10. It is apparent in this case that if reflectance factor is measured only at 75° and 45° (a pair of directions commonly considered for measuring flake finishes at two angles), the measurement would indicate that the specimens match even though the specimens in fact mismatch rather badly over a fairly wide range.

Figure 11:
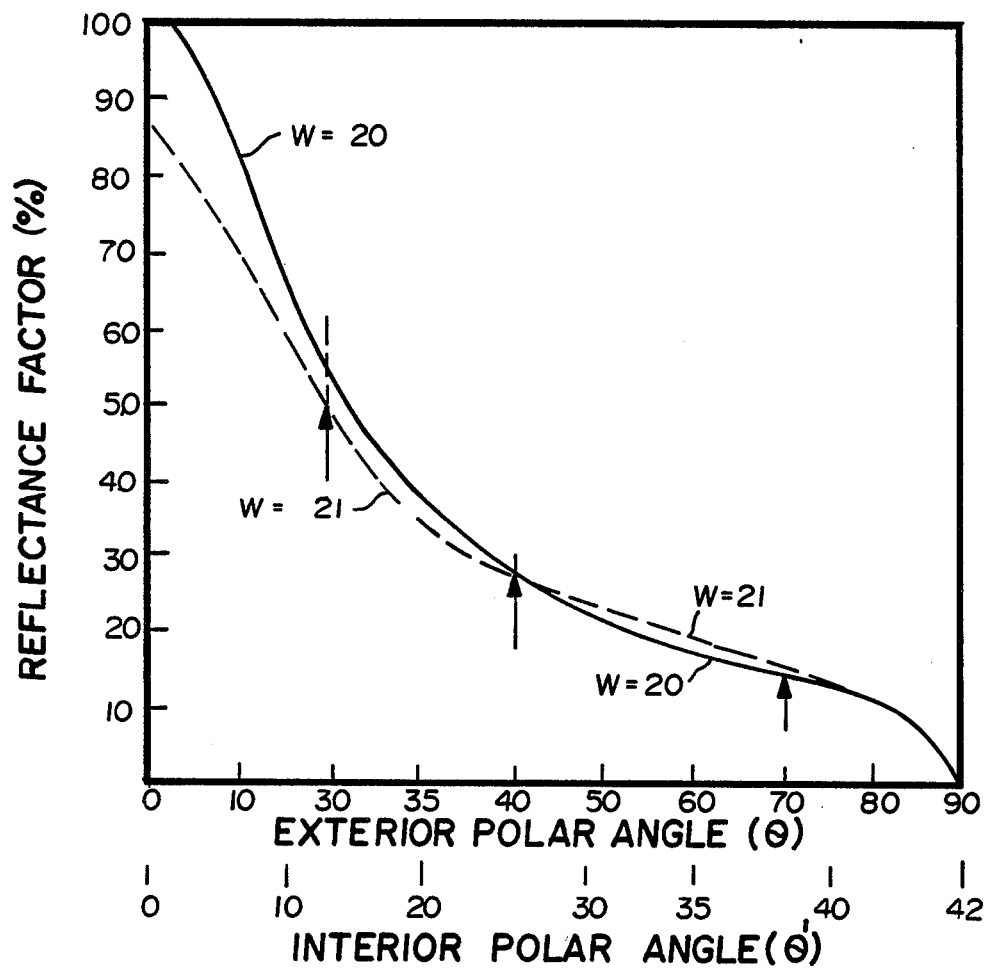
FIG. 11 is a graphical illustration of the reflectance factors shown in FIG. 10 further illustrating the results of measurments made at three different polar angles.

In the preferred embodiment of flake colorimeter 100, the reflected light is measured at three different angles, nominally 20°, 40° and 75° from normal. These three angles have been chosen to provide high sensitivity to all three aspects of the reflectance factor function described in equation (1). These angles are shown with respect to a pair of exemplary reflectance curves in FIG. 11. The measurement at 75° is sensitive mainly to the diffuse component, and the measurements at 40° and 20° are respectively chosen part way up and most of the way up the peak associated with the flake component in order to provide high sensitivity to both the magnitude and the width of the reflectance factor function $F(\theta')$ for the flake component.

It should be emphasized that measurements at three angles are sufficient to determine whether two specimens match only to the extent that differences between model reflectance factor functions for two differing specimens accurately predict the differences between the actual reflection factor functions as obtained from a large series of measurements covering the entire range of angles. Tests on a wide variety of specimens indicate that predictions based on the statistical model of the present invention are excellent.

No specific mention has yet been made of the spectral aspects of the reflectance factor. In the flake colorimeter 100, it has been assumed that, to within a high degree of accuracy, the width of the flake component reflectance factor function is independent of wavelength, and this has been borne out by experimentation. In colorimetric terms, this means that although the luminous reflectance factor of each component, particularly that of the flake component, varies with respect to angle of measurement, the chromaticity of each component taken separately does not vary with angle even though the chromaticity of the combined components varies dramatically.

In summary, measurements at fewer than three different angles are inadequate to specify the color appearance of a flake finish. However, measurements at three appropriate angles fitted with the model of the present invention are sufficient to determine the color of the specimen for all directions of viewing.

(C) DESCRIPTION OF DATA REDUCTION OF THE PRESENT INVENTION

The preferred embodiment flake colorimeter 100 of the present invention uses a data reduction technique to calculate the parameters of the statistical mathematical model expressed in equation 1 from information obtained by measuring a specimen S. The data reduction scheme is performed by processor 108 in the preferred embodiment, and may be implemented using a software program. The calculations involved can be explained in terms of the various control program steps of processor 108 shown in FIG. 12. Certain data required in the operation may be contained in files on a disk (or other magnetic storage medium not shown) and read into a random access memory of processor 108.

In all of the operations involving measurements, the raw bit data are stored by the preferred embodiment flake colorimeter 100 in a 4-dimensional matrix called RAW (T, XX, D, V). The T is used to distinguish between three polar angles (20°, 40° and 75° in the preferred embodiment), the XX is used to distinguish between the three different azimuth angles at which viewers 103 are located, D is used to distinguish between the four colorimetric detectors of the preferred embodiment, and V is used to distinguish between types of data. By expressing raw bit data in these terms, readings may be standardized for each of nine viewing angles separately if desired. All computations are performed as if separate readings are taken for each viewing direction.

In the preferred embodiment, the waggers 118 are opened simultaneously at the three azimuth positions corresponding to each angle of elevation T, and the data obtained are entered into the matrix for each of the three values of XX. Thus, the calculations for each XX value are redundant.

Figure 12:
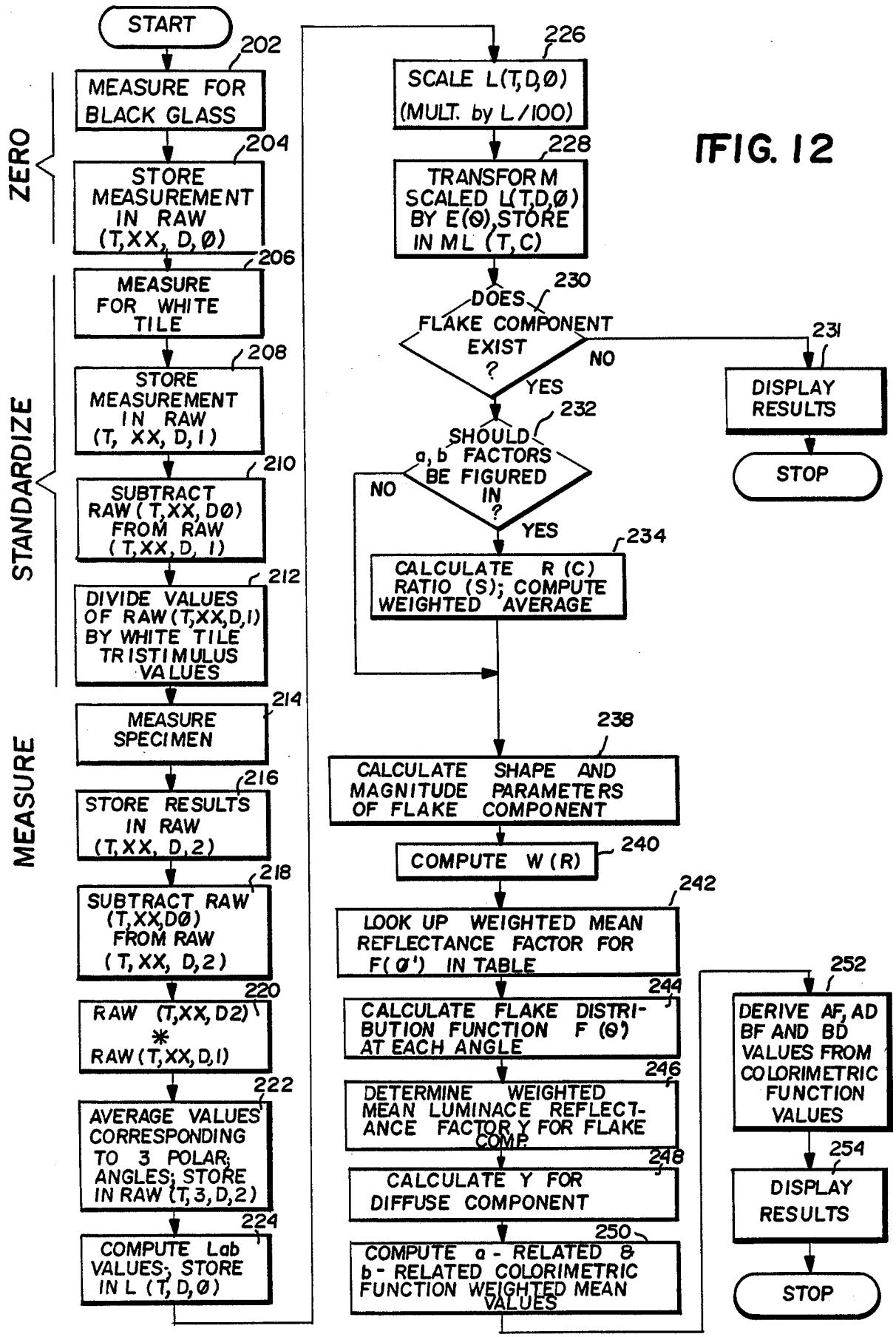
FIG. 12 is a flowchart of exemplary control function steps performed by computer 108 of the embodiment shown in FIG. 1.

The first step in the data reduction occurs during the zero operation (blocks 202, 204 shown in FIG. 12). The raw detector output corresponding to a reading of black glass is stored as is in the matrix RAW (T, XX, D, O) (block 202, 204). There are thirty-six (36) such values corresponding to nine (9) viewing angles and four (4) colorimetric detectors in the preferred embodiment. These values remain unchanged until another zero reading is taken, in which case they are replaced. No attempt is made to store these data permanently, so that if flake colorimeter 100 is restarted for any reason, a new zero reading must be taken.

The second step in the data reduction occurs during a "standardize" operation (blocks 206–212 shown in FIG. 12). The raw bit data for white title is first gathered into RAW (T, XX, D, 1) (blocks 206, 208) and then the raw bit data from the zero standardization (block 204) is subtracted (block 210) to leave in the matrix RAW (T, XX, D, 1) the net signal and bits corresponding to the white tile standard. Finally, the net signal is divided into the appropriate white tile tri-stimulus value for appropriate azimuth angles and the results are stored in the matrix (block 212). Thus, when this calculation is completed, RAW (T, XX, D, 1) contains a calibration factor by which the net raw data for any specimen can be mutiplied in order to get the XA, XB, Y and Z tri-stimulus values for that specimen. These calibration factors are stored unaltered until the next white tile standardization occurs.

The white tile tri-stimulus values calculated as explained above are obtained from the last four of twelve numbers stored in a data file storing constants. These four values are the 0/45 values for X, XB/XA, Y and Z. Also included in this "constants" data file are the emissivities for $\theta = 20°$, 40° and 75°.

The emissivity (transmittance) $E(\theta)$ is used to transform the calculated tri-stimulus values to values inside the dielectric of the paint (where the model of the flake distribution of equation 6 is valid). The emissivity function $E(\theta)$ is calculated in the preferred embodiment for each of the three nominal angles of view according to the following equation:

$$E(\theta) = 1 - \left( \frac{\text{TAN}(\theta - \theta')}{\text{TAN}(\theta + \theta')} \right)^2 + \left( \frac{\text{SIN}(\theta - \theta')}{\text{SIN}(\theta + \theta')} \right)^2 / 2 \qquad (6a)$$

The interior polar angle can be calculated according to the relation:

$$\theta' = \text{Arcsin} \frac{\text{Sin } \theta}{N} \qquad (6b)$$

where N is the index of refraction of the dielectric of the finish with respect to air.

The XA and XB values at 45° are calculated first from the X and XA/XB data supplied, and these values are used for the tri-stimulus values at 40°. In principle, these values should be about 0.4% lower because the emissivity at 40° is that much larger than the emissivity at 45°, but this approximation is adequate for the purposes of the preferred embodiment. The tri-stimulus values at the other two polar angles are calculated by multiplying the corresponding 40° tri-stimulus value by the quotient of the emissivity at the given angle divided by the emissivity at 40°.

When a measurement of a specimen is made (blocks 214-254 shown in FIG. 12), the raw bit data are entered in the matrix RAW (T, XX, D, 2) (blocks 214, 216). Each value is then converted to the net signal value by subtracting the corresponding black glass signal stored in RAW (T, XX, D, 0) (block 218). That net signal is then converted to tri-stimulus values by multiplying by the calibration factors stored in RAW (T, XX, D, 1) (block 220). The matrix RAW (T, XX, D, 2) then contains, for the specimen just measured, four tri-stimulus values for each of the nine directions of view (corresponding to the nine viewers 103). The average of the three values corresponding to each polar angle is calculated and stored in RAW (T, 3, D, 2) (block 222). The tri-stimulus values stored in RAW (T, 3, D, 2) are used by the preferred embodiment for all remaining calculations for the specimen and are retained unaltered until another reading is made.

The L a b values are calculated from the tri-stimulus values stored in RAW (T, 3, D, 2) in a normal, conventional way and stored in a matrix L (T, D, 0) (block 224), where T (as before) represents the polar angles, and L is stored for D=0, a is stored D=1 and b is stored D=2. The third dimension 0 represents the fact that the values are being treated as specimen values. Standard values are recalled from memory into L (T, D, 1) for purposes of calculating differences. At the end of this computational procedure, the L a b values are permanently stored by processor 108 (e.g., on a disk or the like) as the goniometric values for that specimen.

In order to permit faster calculation of the parameters of the model expressed in equation 1 above, the modeled data is calculated by means of table lookup and interpolation. The first step in the modeling procedure is to scale the L a b values by multiplying by L/100 (in which case L is replaced by $Y/Y_0$ and the a and b components become linear in X, Y and Z) (block 226). The color coordinates so calculated are then transformed by dividing by the appropriate value of the emissivity function (E$\theta$) in order to obtain their magnitudes as they would be seen before internal reflection at the medium boundary (block 228). These resulting values are stored in a Table ML (T, C) (block 228), where T represents the polar angle and C represents the colorimetric coordinate.

The next step is to establish the value of W for the flake distribution represented by the colorimetric data. On what data this value depends is determined in the preferred embodiment based on the X, Y and Z data contained in the matrix RAW (T, 3, D, 2) calculated as described above (block 222). If the Y value at 20° is less than 5% greater than the Y value at 75° (both evaluated internally), it is assumed that the flake contribution does not exist and that the measured specimen is ordinary diffusely pigmented paint (block 230). In that case, no flake component is calculated for the model. Similarly, if the difference between the Y value at 20° and the Y at 75° (evaluated internally) is less than 4 on an absolute basis, the preferred embodiment treats the finish as strictly diffuse (block 230).

If, in the tests described above, it is determined that a flake component does exist (block 230), a further test is performed to determine whether to include an a-related and b-related component in calculating the width factor W. Only if the absolute value of $X/X_O - Y/YO$ is greater than 0.01 will the preferred embodiment use a-related colorimetric values in determining the width factor W (block 232). Similarly, only if the absolute value of $Y/Y_O - Z/ZO$ is greater than 0.01 will the b-related colorimetric values be used in determining W (block 232).

Of the colorimetric values to be included in calculating the width factor W, a ratio R(C) is calculated (block 234) as follows:

$$R(C) = \frac{(ML(20°, C.) - ML(75°, C.))}{(ML(40°, C.) - ML(75°, C.))} \quad (7)$$

Figure 13:
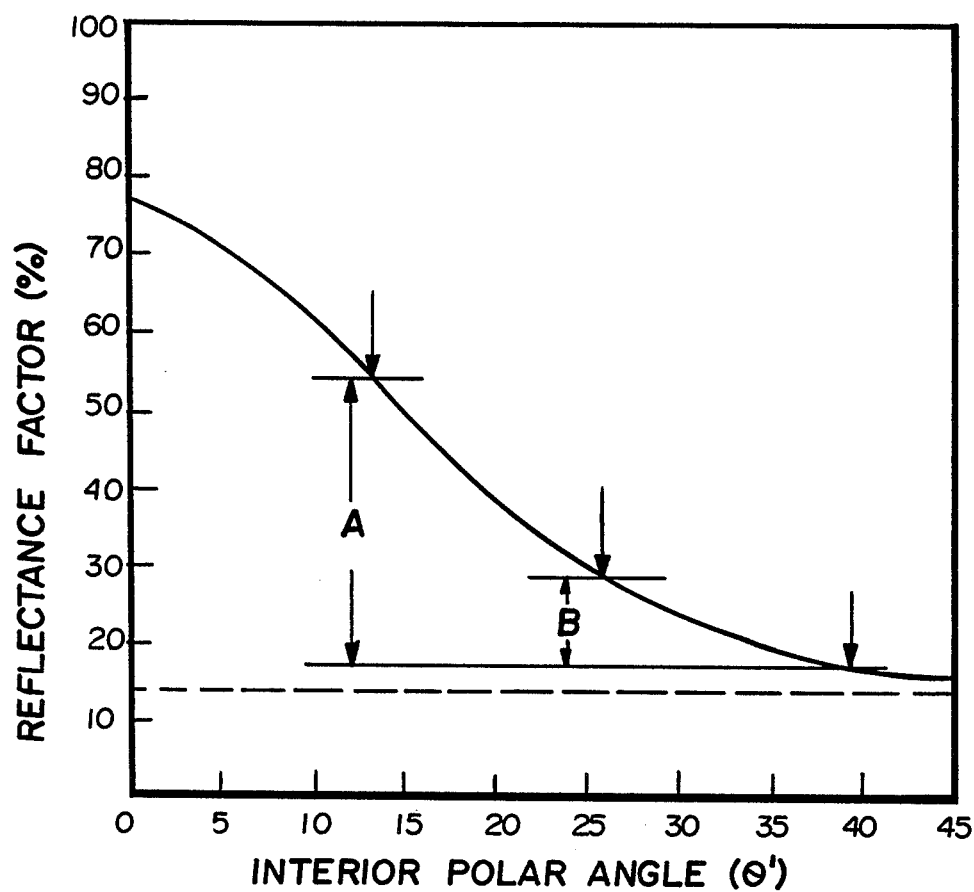
FIG. 13 is a graphical illustration of the manner in which reflectance factor is used to determine the flake component of the statistical model in accordance with the present invention.

The weighted average of these ratios R(C), using the factor (ML(20°, C.)−ML(40°, C.) as a weighting factor, is a ratio R (reflectance) of which W is a monotonically decreasing function. FIG. 13 graphically depicts R(C) for a colorimetric value denoted by C.

With all values determined internally, the diffuse reflectance factor is assumed to be independent of polar angle. Therefore, the shape of the total reflectance curve F ($\theta'$) above a constant background depends on the flake component alone.

The ratio A/B of the two differences $$A = F(13.2°) - F(40.1°)$$

and $$B = F(25.4°) - F(40.1°)$$

is calculated next (block 238). This ratio ("SHAPE") is characteristic of the shape of the flake component distribution. Once the shape of the distribution has been determined, the sum A+B is calculated (block 238), this value being characteristic of the magnitude of a flake distribution having that shape. The total reflectance factor curve R (F($\theta'$)) is estimated in this way (block 238).

The value of the width factor W is calculated from the value of R by means of a table-lookup and interpolation in the preferred embodiment. A lookup table is stored in a non-volatile memory which can be read by processor 108. Exemplary data for this table is set forth below in Table 1:

TABLE 1

| R | W | K0 | K1 | K2 | K3 |
|---|---|---|---|---|---|
| 1.51272 | 100.367 | −39.3758 | 14.8992 | −2.50112 | .0222963 |
| 1.53502 | 73.3895 | −32.2726 | 18.7604 | −5.68901 | .0421268 |
| 1.57714 | 54.1883 | −22.5773 | 12.4794 | −3.56842 | .0804737 |
| 1.65762 | 40.5219 | −17.7789 | 11.6343 | −3.58243 | .171884 |
| 1.8295 | 30.7949 | −16.0417 | 14.6227 | −5.50409 | .524453 |
| 2.35395 | 23.8718 | −9.79514 | 7.71346 | −2.84579 | 1.55265 |
| 3.90661 | 18.9444 | −5.61076 | 2.90439 | −.800729 | 2.99821 |
| 6.90482 | 15.4373 | −4.28444 | 2.55973 | −.771445 | 5.8279 |
| 12.7327 | 12.9411 | −3.15316 | 2.01826 | −.641724 | 12.4221 |
| 25.1548 | 11.1645 | −2.21091 | 1.38514 | −.438726 | 26.362 |
| 51.5169 | 9.9 | −1.50475 | .871311 | −.266562 | 52.4148 |
| 103.932 | 9 | 0 | 0 | 0 | 0 |

Each row of Table 1 has six entries: a value of R (the rows are in order of increasing R); the corresponding value of W; and four coefficients (K0−K3) of a polynominal spline function used to interpolate W to the next value of R.

The following equation is used to calculate the width factor W from the values stored in the lookup table (Table 3):

$$W(R) = K0 + (K1*R) + (K2*R^2) + (K3*R^3) \quad (8)$$

W(R) is continuous with a continuous first derivative over the range of R covered (1.486 through 88.618). That range of R corresponds to a range of W from 9° to 100° (which extends in both directions considerably beyond the range of 13° to 22° within which all specimens measured to date have fallen). By finding the range in which R falls, equation (8) is used to calculate the value of W (block 240) which is outputted by processor 108 as the WIDTH statistical model parameter.

A weighted mean reflectance factor for the corresponding $F(\theta')$ function is then calculated from the width value W so determined, once again using table-lookup and interpolation as a means of increasing the speed at which processor 108 performs the required calculations (block 242).

Since it is desirable to report the mean value of Y taken over the hemisphere of exterior viewing, the integral of equation 6 multiplied by $E(\theta)$ taken over the hemisphere is used. In this case, the weighting factor is the usual radiometric $\sin(\theta) * \cos(\theta)$ product. As before, there are six entries in each group in the stored table as contained in a permanent data file. Exemplary values for this permanent data file are set forth in Table 2 below:

TABLE 2

| W | FBAR | J0 | J1 | J2 | J3 |
|---|------|------|------|------|------|
| 9 | .647584 | .0507327 | $-2.38091*10^{-3}$ | $-2.67632*10^{-4}$ | .9 |
| 9.9 | .695688 | .063461 | $-5.18052*10^{-3}$ | $-9.22754*10^{-4}$ | 1.2645 |
| 11.1645 | .753026 | .0707161 | $-.0126767$ | $-2.40454*10^{-3}$ | 1.77662 |
| 12.9411 | .808661 | .0535993 | $-.0328413$ | $-3.57212*10^{-3}$ | 2.49615 |
| 15.4373 | .825846 | $-.320336$ | $-.0771917$ | .0157751 | 3.5071 |
| 18.9444 | .732396 | $-.195424$ | $-.0246238$ | .0507408 | 4.92747 |
| 23.8718 | .56309 | $-.12989$ | .182499 | $-.0540387$ | 6.9231 |
| 30.7949 | .561659 | .102522 | .0230584 | $-.019607$ | 9.72695 |
| 40.5219 | .667663 | .126237 | $-.038713$ | $5.34399*10^{-3}$ | 13.6664 |
| 54.1883 | .760531 | .0911037 | $-.0353878$ | $6.89071*10^{-3}$ | 19.2012 |
| 73.3895 | .823137 | .0576055 | $-.0251637$ | $5.68836*10^{-3}$ | 26.9777 |
| 100.367 | .861267 | 103.065 | 0 | 0 | 0 |

There are six entries in each row of Table 2. These six entries are: W in order of increasing value of W; FBAR, the weighted mean value of $F(\theta')$ for that W; and coefficients J0-J3 for interpolating over the interval to the next point according to the following equation:

$$FBAR(W) = J0 + (J1*W) + (J2*W^2) + (J3*W^3) \quad (9)$$

Once W has been determined (by block 240), the flake distribution function $F(\theta')$ can be calculated for each of the angles of observation (block 244). By using appropriate ratios of the measured $Y(\theta)$ values to the calculated function $F(\theta')$, the weighted mean luminous reflectance YF corresponding to the flake component can be determined (block 246). The preferred embodiment uses a calculation expressed in terms of outside angles, given by the following equation:

$$YF = \frac{FBAR * (Y(20°) + Y(40°) - 2Y(75°))}{F(20°) + F(40°) - 2F(75°)} \quad (10)$$

The Y value corresponding to the diffuse component is then calculated (block 248) as:

$$YD = Y(70°) - YF*F(75°)/FBAR \quad (11)$$

By a similar procedure, weighted mean values of the a-related and b-related colorimetric functions are calculated (block 250). These colorimetric function values are then divided by the corresponding weighted mean Y values (YF or YD) and multiplied by 100 to yield scaled AF, AD, BF and BD values (block 252). The values W (calculated by block 240); AF, AD, BF, BD (calculated by block 252); YF (calculated by block 246); and YD (calculated by block 248) are then output by processor 108 and printed on printer 112 (or displayed on display 110) (block 254).

(D) MAKING USE OF THE DATA OBTAINED BY THE PREFERRED EMBODIMENT

The preferred embodiment of flake colorimeter 100 of the present invention produces output data in two distinct modes. Each mode is intended to serve a particular application purpose.

The first mode is called the goniometric mode. In this mode, L a b data (opponent-colors color scale values corresponding to Lightness, Redness/Greenness, and Yellowness/Blueness, respectively), are output for each of the nominal viewing angles. Table 3 set forth below shows representative specimen goniometric mode data as printed by printer 112 of the preferred embodiment shown in FIG. 1:

TABLE 3

| SPC. BB22A | | STD. BB22 | | SPC. BB22A | |
|---|---|---|---|---|---|
| 20 deg. | | 20 deg. | | 20 deg. | |
| L = | 36.80 | L = | 36.78 | DL = | 0.02 |
| a = | $-12.81$ | a = | $-12.30$ | Da = | $-0.51$ |
| b = | $-33.67$ | b = | $-33.58$ | Db = | $-0.10$ |
| 40 deg. | | 40 deg. | | 40 deg. | |
| L = | 25.35 | L = | 25.49 | DL — | $-0.14$ |
| a = | $-5.55$ | a = | $-5.41$ | Da = | $-0.14$ |
| b = | $-29.34$ | b = | $-29.32$ | Db = | $-0.02$ |
| 75 deg. | | 75 deg. | | 75 deg. | |
| L = | 16.12 | L = | 16.25 | DL = | $-0.13$ |
| a = | $-1.30$ | a = | $-1.27$ | Da = | $-0.03$ |
| b = | $-22.80$ | b = | $-22.88$ | Db = | 0.08 |

The purpose of these data is to indicate the color appearance and, more importantly to most applications, the magnitude and direction of differences in color appearance. These data are for an average over the viewed area (approximately one inch in diameter in the preferred embodiment).

A match between specimens for these data does not mean that the appearance will match with respect to spatial arrangement of the flakes over the area viewed. Rather, the match will be on the average. However, if the size of the flakes is determined to be the same for both specimens by some other means of measurement, and if the distribution of the flakes over the surface is reasonably uniform, equal readings indicate that the product should look alike under any circumstances. In the event that the goniometric data do not match, the values will indicate in terms of visual assessment how large the difference is.

In the other mode of output of the preferred embodiment flake colorimeter 100, the data concerning the statistical model set forth in equation (1) above is given. Table 4 below sets forth representative specimens of the modeled mode data as printed by printer 112 of the embodiment shown in FIG. 1:

TABLE 4

| SPC. BB22A | | STD. BB22 | | SPC. BB22A | |
|---|---|---|---|---|---|
| FLAKE | | FLAKE | | FLAKE | |
| Y = | 4.34 | Y = | 4.35 | DY = | −0.01 |
| A = | −41.16 | A = | −39.76 | DA = | −1.40 |
| B = | −79.71 | B = | −79.17 | DB = | −0.54 |
| WIDTH = | | WIDTH = | | DWIDTH = | |
| 20.32 deg. | | 20.44 deg. | | −0.12 deg. | |
| DIFFUSE | | DIFFUSE | | DIFFUSE | |
| Y = | 2.44 | Y = | 2.47 | DY = | −0.03 |
| A = | −0.40 | A = | −0.25 | DA = | −0.15 |
| B = | −155.66 | B = | −155.36 | DB − | −0.31 |

For the flake and diffuse components, the mean hemispherical luminous reflectance (Y) and two chromaticity coordinates (A, B) are given. In the preferred embodiment, the chromaticity coordinates are expressed in terms of A and B, the a and b components being scaled so that L will be normalized (i.e., 100). This scaling can be changed, of course, should better indicators of chromaticity be decided upon. In addition, the width W associated with the error function part of $F(\theta')$ (see equation 3) is also given as a parameter to indicate the degree to which the flakes depart from lying flat with respect to the media surface.

The modeled mode of output provided by the present invention is very useful in the area of quality control, paint matching, and the like, since the output is closely connected to the physical structure of the paint. Thus, feedback for the operator of the finish application system can be based on this data.

For example, a low value for the flake luminous reflectance combined with a high value for the diffuse luminous reflectance suggests that there are too few flakes in the mixture. Such increase in the diffuse component results from less hiding by the flakes. Further evidence of this situation might be obtained from observing the chromaticity of the diffuse component for changes characteristic of too few flakes, with the corresponding reduction in neutral reflections.

A simultaneous decrease in both flake and diffuse components suggests poor reflection on the part of the flakes or excessive colorant in the pigmentation. Evidence from the chromaticity coordinates helps sort out which of these two conditions exists.

The width factor W may be correlated with a number of conditions (e.g., surface tension of the wet vehicle, film thickness, spray-gun pressure and the like).

Through cooperative work with those actually applying the paints, such correlations between the modeled data and the conditions of application and the composition of the paint can be developed to the point where the modeled output can be expressed in terms of suggested remedies instead of (or in addition to) direct numerical outputs of the model parameters.

(E) EXEMPLARY RESULTS FROM TEST MEASUREMENTS

Exemplary results from actual measurements performed on real specimens will now be presented. The optical characteristics of a variety of specimens were measured with a conventional goniospectrophotometer, and the L, a and b colorimetric values were obtained. Then, the preferred embodiment flake colorimeter 100 of the present invention was used to measure the optical characteristics of the same specimens, and the preferred embodiment flake colorimeter calculated the L, a and b parameters as well as the parameters of the statistical model in accordance with the present invention. Further data was obtained by fitting the modeling function of the present invention (equation 1) at three angles to the goniometric data obtained from the goniospectrophotometer. Finally, L, a, b data at the 20°, 40° and 75° measurement angles of the preferred embodiment were interpolated from the results of the goniospectrophotometer for comparison with the L, a, b values measured by the preferred embodiment flake colorimeter 100.

Twenty-six widely differing specimens were measured and tested. The results of five of the twenty-six specimens are presented here. The presented results are typical of what was found in comparing goniospectrophotometric data to modeled data for the twenty-six widely differing specimens.

The first two specimens (690 and 691) discussed are gray metallics which were designed to mismatch badly with the respect to the goniometric reflectance factor function, although at first glance they appear to be similar. The third and fourth specimens (692 and 693) are unsaturated light-brown specimens which were intended to match, but did not match exactly. The fifth specimen (687) consists of golden flakes in a transparent layer over a red diffuse sublayer.

E(1) EXAMPLE 1

SPECIMENS 690 AND 691

The following Table 5 sets forth goniospectrophotometric data (L, a, b values), for a source directed normal to the specimen surface, for specimen 691 (a gray metallic) together with differences between that data and the goniospectrophotometric data measured for "STD" (standard) specimen 690 (a different gray metallic):

TABLE 5

| VIEW | L | a | b | DELTAS FROM STD | | |
|---|---|---|---|---|---|---|
| 10 | 111.71 | −0.57 | −0.53 | −18.64 | 1.37 | −0.87 |
| 15 | 102.39 | −0.51 | −0.60 | −16.37 | 1.09 | −0.57 |
| 20 | 93.30 | −0.47 | −0.72 | −13.66 | 0.83 | −0.57 |
| 25 | 84.57 | −0.50 | −0.81 | −10.72 | 0.66 | −0.42 |
| 30 | 76.68 | −0.47 | −0.92 | −8.13 | 0.39 | −0.33 |
| 35 | 69.57 | −0.47 | −0.98 | −5.40 | 0.27 | −0.31 |
| 40 | 63.57 | −0.43 | −0.98 | −3.16 | 0.05 | −0.36 |
| 45 | 58.46 | −0.47 | −0.98 | −1.02 | −0.05 | −0.34 |
| 50 | 54.19 | −0.47 | −0.99 | 0.84 | −0.16 | −0.39 |
| 55 | 50.68 | −0.41 | −0.92 | 2.33 | −0.26 | −0.46 |
| 60 | 47.74 | −0.43 | −0.90 | 3.54 | −0.38 | −0.51 |
| 65 | 44.98 | −0.49 | −0.89 | 4.47 | −0.39 | −0.48 |
| 70 | 42.24 | −0.51 | −0.81 | 5.22 | −0.31 | −0.57 |
| 75 | 39.19 | −0.55 | −0.71 | 5.46 | −0.37 | −0.59 |
| 80 | 34.91 | −0.49 | −0.65 | 5.47 | −0.29 | −0.64 |

Figure 14:
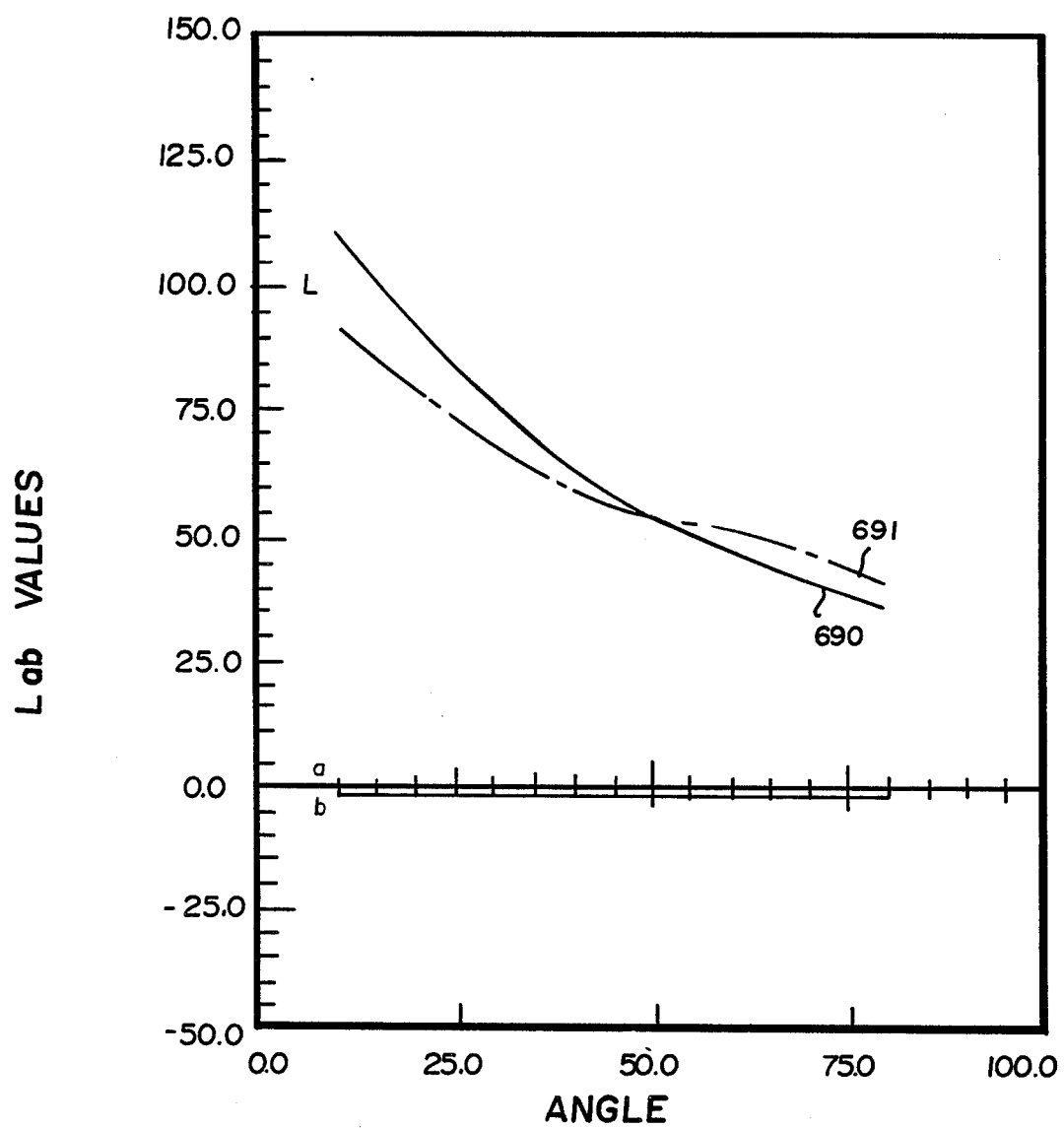
FIG 14 is a graphical illustration of data obtained from goniospectrophotometric measurements of exemplary specimens 690 and 691.

FIG. 14 is a graphical illustration of the goniophotometric data measured for specimens 690 and 691 plotted along the same set of axes. As can be seen, these two specimens mismatch rather badly with respect to the goniometric reflectance factor function.

Table 6 below presents a comparison of the measured goniometric data for specimen 690 to the data obtained by fitting the modeling function (equation 1) at three angles:

TABLE 6

| ANGLE (deg) | L-EXT GONIO | L-EXT MODEL-G | a-EXT GONIO | a-EXT MODEL-G | b-EXT GONIO | b-EXT MODEL-G |
|---|---|---|---|---|---|---|
| 10 | 112.82 | −0.69 | −0.58 | −0.01 | −0.53 | −0.31 |
| 15 | 103.41 | −0.26 | −0.52 | −0.06 | −0.61 | −0.21 |
| 20 | 94.23 | 0.02 | −0.48 | −0.09 | −0.72 | −0.07 |
| 25 | 85.41 | 0.28 | −0.50 | −0.06 | −0.82 | 0.05 |
| 30 | 77.44 | 0.27 | −0.47 | −0.09 | −0.93 | 0.17 |
| 35 | 70.26 | 0.23 | −0.48 | −0.09 | −0.99 | 0.24 |
| 40 | 64.20 | −0.02 | −0.44 | −0.13 | −0.99 | 0.24 |
| 45 | 59.04 | −0.21 | −0.47 | −0.11 | −0.99 | 0.23 |
| 50 | 54.72 | −0.32 | −0.48 | −0.12 | −1.00 | 0.23 |
| 55 | 51.18 | −0.41 | −0.41 | −0.20 | −0.93 | 0.16 |
| 60 | 48.21 | −0.44 | −0.43 | −0.19 | −0.91 | 0.13 |
| 65 | 45.43 | −0.27 | −0.50 | −0.12 | −0.90 | 0.13 |
| 70 | 42.66 | −0.06 | −0.51 | −0.09 | −0.82 | 0.07 |
| 75 | 39.58 | 0.05 | −0.56 | −0.02 | −0.71 | −0.01 |
| 80 | 35.26 | 0.14 | −0.50 | −0.03 | −0.66 | 0.00 |

The following Table 7 presents a comparison of the measured goniometric data for specimen 691 with the data obtained by fitting the modeling function at three angles:

TABLE 7

| ANGLE (deg) | L-EXT GONIO | L-EXT MODEL-G | a-EXT GONIO | a-EXT MODEL-G | b-EXT GONIO | b-EXT MODEL-G |
|---|---|---|---|---|---|---|
| 10 | 93.99 | −0.49 | 0.80 | −0.05 | −1.41 | 0.20 |
| 15 | 86.88 | −0.08 | 0.58 | −0.05 | −1.19 | −0.03 |
| 20 | 80.43 | 0.00 | 0.36 | −0.06 | −1.30 | 0.07 |
| 25 | 74.59 | −0.02 | 0.17 | −0.09 | −1.24 | −0.01 |
| 30 | 69.23 | 0.10 | −0.08 | −0.06 | −1.26 | −0.01 |
| 35 | 64.81 | −0.01 | −0.21 | −0.13 | −1.31 | 0.00 |
| 40 | 61.01 | 0.01 | −0.39 | −0.12 | −1.36 | 0.02 |
| 45 | 58.01 | −0.08 | −0.52 | −0.13 | −1.33 | −0.04 |
| 50 | 55.57 | −0.12 | −0.64 | −0.14 | −1.39 | 0.00 |
| 55 | 53.53 | −0.11 | −0.68 | −0.19 | −1.40 | 0.00 |
| 60 | 51.79 | −0.13 | −0.81 | −0.11 | −1.42 | 0.02 |
| 65 | 49.95 | −0.02 | −0.90 | −0.06 | −1.38 | 0.00 |
| 70 | 47.93 | −0.03 | −0.83 | −0.13 | −1.40 | 0.04 |
| 75 | 45.09 | 0.02 | −0.93 | −0.01 | −1.31 | 0.02 |
| 80 | 40.79 | −0.15 | −0.79 | −0.07 | −1.30 | 0.13 |

As can be seen from the results set forth in Tables 6 and 7 above, the comparison between the two sets of data is quite good at all angles except 10° and, to a lesser extent, 15°. This difference is attributed to the fact that some of the surface reflection not included in the model is measured by the goniospectrophotometer at the angles of 10° and 15°.

The following Table 8 sets forth the parameters of the statistical model (equation 1) of the present invention as calculated from the goniospectrophotometric data obtained for specimen 690:

TABLE 8

| FLAKE | |
|---|---|
| Y = | 30.65 |
| A = | −0.44 |
| B = | −0.43 |
| WIDTH | 20.44 deg. |
| DIFFUSE | |
| Y = | 15.24 |
| A = | −1.45 |
| B = | −1.80 |

Table 9 below sets forth the actual model parameters measured for specimen 690 using the filter colorimetry of the preferred embodiment flake colorimetric 100 of the present invention and calculated by the preferred embodiment:

TABLE 9

| FLAKE | |
|---|---|
| Y = | 30.48 |
| A = | 2.04 |
| B = | −4.37 |
| WIDTH = | 20.24 deg. |
| DIFFUSE | |
| Y = | 15.40 |
| A = | −0.38 |
| B = | −3.29 |

As can be seen, the Y values of Tables 8 and 9 correspond quite closely, particularly considering that measurements performed by two different instruments (the preferred embodiment flake colorimeter 100 and a conventional goniospectrophotometer) are being compared. These instruments are calibrated differently and measure somewhat different areas on the specimen subject to statistical variations.

Table 10 below sets forth goniometric data, derived from the spectrophotometric measurements for sample 690, interpolated for the 20°, 40° and 75° nominal angles measured by preferred embodiment flake colorimeter 100:

TABLE 10

| 18.75 deg. | |
|---|---|
| L = | 96.50 |
| a = | −0.60 |
| b = | −0.65 |
| 38.50 deg. | |
| L = | 65.92 |
| a = | −0.52 |
| b = | −0.97 |

TABLE 10-continued

| | 73.00 deg. |
|---|---|
| L = | 40.91 |
| a = | −0.59 |
| b = | −0.74 |

Table 11 lists goniometric L, a, b values measured by preferred embodiment flake colorimeter 100 of the present invention for sample 690:

TABLE 11

| | 20 deg. |
|---|---|
| L = | 96.50 |
| a = | 1.97 |
| b = | −3.04 |
| | 40 deg. |
| L = | 66.01 |
| a = | 0.15 |
| b = | −4.07 |
| | 75 deg. |
| L = | 40.82 |
| a = | 0.04 |
| b = | −1.43 |

The agreement between the luminance (L) values show in Tables 10 and 11 above is quite good considering the problems of comparing the measurements of two different instruments as discussed above. The agreement, both on an absolute and on a relative basis, is not quite as good between the a and b values. Part of the problem on a absolute basis is simply the difference between filter colorimetry and spectrophotometric colorimetry. However, the bulk of the problem is probably due to angular differences in sampling by the fiber bundles of viewers 103 with respect to the colorimetric detectors. The best way to overcome this problem is to use a sphere as a mixing element.

Tables 12 and 13, below, set forth the parameters of the model of the present invention computed from goniospectrophotometric data for sample 691, and the model parameters calculated by preferred embodiment flake colorimeter 100 from measurements of specimen 691, respectively.

TABLE 12

| | FLAKE | |
|---|---|---|
| Y = | 16.71 | |
| A = | 1.54 | |
| B = | −0.87 | |
| WIDTH = | 19.98 deg. | |
| | DIFFUSE | |
| Y = | 22.91 | |
| A = | −2.06 | |
| B = | −2.85 | |

TABLE 13

| | FLAKE | |
|---|---|---|
| Y = | 16.73 | |
| A — | 4.35 | |
| B = | −3.42 | |
| WIDTH | 20.03 deg. | |
| | DIFFUSE | |
| Y = | 22.57 | |
| A = | −8.86 | |
| B — | −4.22 | |

Tables 14 and 15 below respectively list goniometric data interpolated from spectrophotometric data measured for specimen 691 at the three nominal viewing angles of preferred embodiment flake colorimeter 100, and goniometric values produced by the preferred embodiment based on spectrophotometric measurements of specimen 691.

TABLE 14

| | 18.75 deg. |
|---|---|
| L = | 81.99 |
| a = | 0.32 |
| b = | −1.23 |
| | 38.50 deg. |
| L = | 62.07 |
| a = | −0.41 |
| b = | −1.32 |
| | 73.00 deg. |
| L = | 46.37 |
| a = | −0.95 |
| b = | −1.32 |

TABLE 15

| | 20 deg. |
|---|---|
| L = | 81.60 |
| a = | 2.06 |
| b = | −2.53 |
| | 40 deg. |
| L = | 62.01 |
| a = | −0.10 |
| b = | −3.08 |
| | 75 deg. |
| L = | 46.08 |
| a = | −0.62 |
| b = | −1.92 |

Much can be learned about the differences in specimens 690 and 691 by comparing the results set forth in Tables 9 and 13 (the parameters of the model of the present invention as measured and calculated by preferred embodiment flake colorimeter 100). Although there is a slight difference in the width (W) factors of specimens 690 and 691, this is not nearly as significant as the differences in the flake and diffuse components. One can deduce from the data that specimens 690 and 691 were constructed by using a diffuse substrate which had approximately the same reflectance as the flakes, and by simply including more flakes in specimen 690 than in specimen 691. Physical examination of these two specimens verified the difference in the number of flakes per unit area.

E(2) EXAMPLE 2

SPECIMENS 692 AND 693

Figure 15:
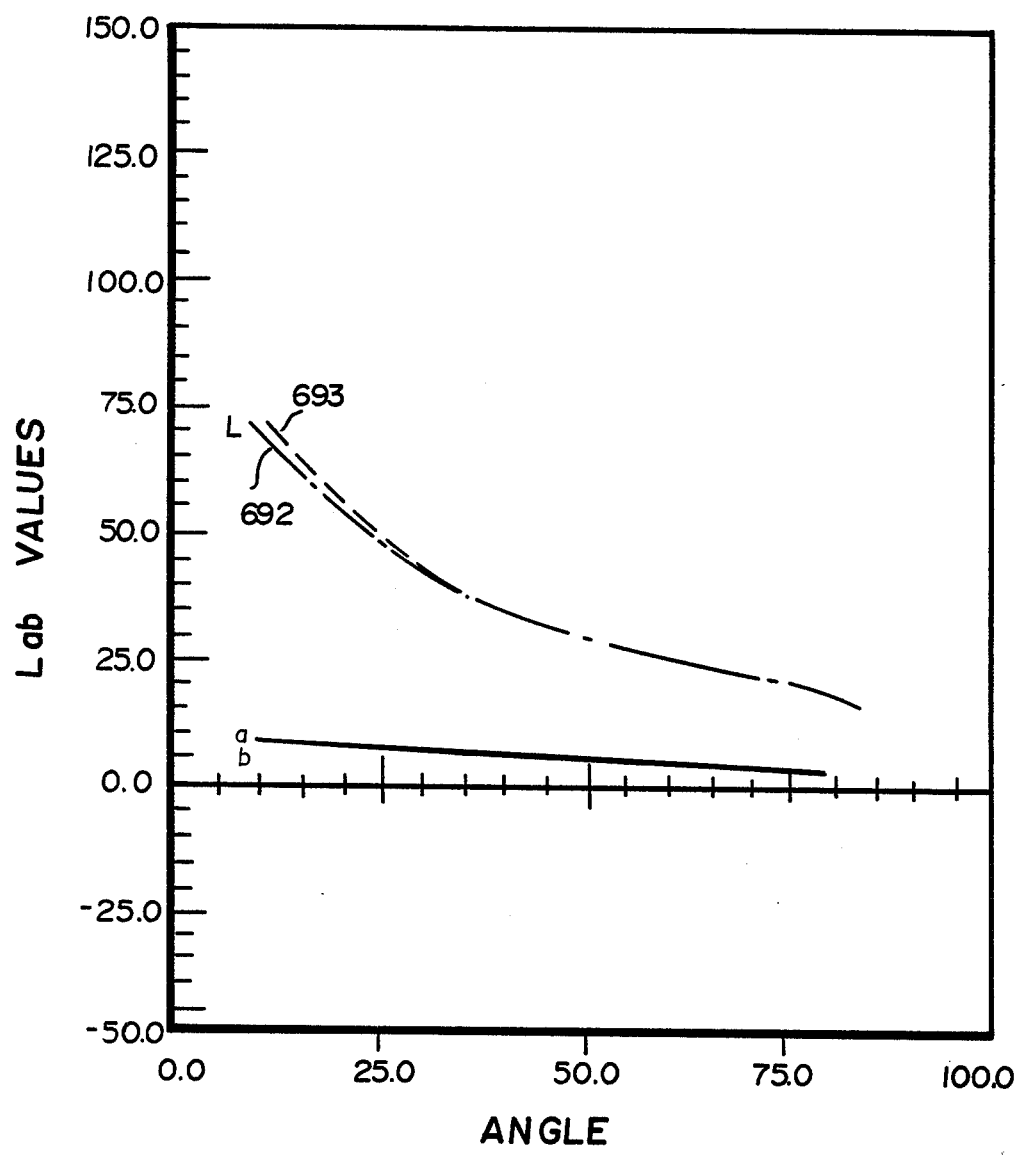
FIG. 15 is a graphical illustration of the results of goniospectrophotometric measurement of two additional exemplary specimens 692 and 693.

As mentioned above, specimens 692 and 693 are unsaturated light-brown specimens which were intended to match, but did not match exactly. Table 16 below compares the goniospectrophotometric data for samples 692 and 693, while FIG. 15 plots the two sets of goniospectrophotometric data on common axes.

TABLE 16

| VIEW | L | a | b | DELTAS FROM STD | | |
|---|---|---|---|---|---|---|
| 10 | 70.01 | 7.60 | 8.06 | 2.95 | 0.20 | 0.34 |
| 15 | 61.97 | 7.00 | 7.25 | 1.70 | 0.21 | 0.24 |
| 20 | 54.84 | 6.40 | 6.54 | 0.88 | 0.09 | 0.03 |
| 25 | 48.35 | 5.75 | 5.76 | 0.43 | 0.07 | 0.03 |
| 30 | 42.72 | 5.20 | 5.14 | 0.32 | 0.05 | 0.03 |
| 35 | 38.16 | 4.79 | 4.65 | 0.07 | −0.02 | −0.09 |
| 40 | 34.53 | 4.40 | 4.29 | −0.26 | −0.08 | −0.12 |
| 45 | 31.30 | 4.12 | 3.85 | −0.28 | −0.07 | −0.09 |
| 50 | 28.52 | 3.84 | 3.63 | −0.20 | −0.03 | −0.16 |
| 55 | 26.40 | 3.59 | 3.30 | −0.24 | −0.06 | −0.11 |
| 60 | 24.58 | 3.52 | 3.12 | −0.19 | −0.07 | −0.18 |
| 65 | 23.11 | 3.34 | 2.87 | −0.25 | −0.06 | −0.12 |
| 70 | 21.74 | 3.12 | 2.61 | −0.35 | −0.12 | −0.22 |

TABLE 16-continued

| VIEW | L | a | b | DELTAS FROM STD | | |
|---|---|---|---|---|---|---|
| 75 | 20.19 | 2.67 | 2.56 | −0.45 | 0.19 | −0.24 |
| 80 | 18.02 | 2.71 | 1.96 | −0.19 | −0.19 | −0.31 |

Table 17 presents a comparison of the goniospectrophotometric data for sample 692 with the data obtained by fitting the modeling function (equation 1) at three angles, while Table 18 below provides similar data for specimen 693.

TABLE 17

| ANGLE | L-EXT | | a-EXT | | b-EXT | |
|---|---|---|---|---|---|---|
| (deg) | GONIO | MODEL-G | GONIO | MODEL-G | GONIO | MODEL-G |
| 10 | 70.70 | −1.29 | 7.67 | 0.31 | 8.14 | 0.18 |
| 15 | 62.58 | −0.37 | 7.07 | 0.12 | 7.33 | 0.14 |
| 20 | 55.39 | 0.11 | 6.47 | −0.01 | 6.61 | 0.06 |
| 25 | 48.83 | 0.48 | 5.81 | −0.02 | 5.82 | 0.12 |
| 30 | 43.15 | 0.60 | 5.25 | −0.06 | 5.19 | 0.10 |
| 35 | 38.54 | 0.34 | 4.84 | −0.16 | 4.70 | 0.02 |
| 40 | 34.88 | −0.14 | 4.44 | −0.20 | 4.33 | −0.10 |
| 45 | 31.61 | −0.27 | 4.16 | −0.26 | 3.89 | −0.05 |
| 50 | 28.81 | −0.20 | 3.87 | −0.25 | 3.66 | −0.14 |
| 55 | 26.66 | −0.20 | 3.63 | −0.22 | 3.33 | −0.06 |
| 60 | 24.82 | −0.08 | 3.56 | −0.32 | 3.15 | −0.08 |
| 65 | 23.34 | −0.03 | 3.38 | −0.29 | 2.90 | 0.00 |
| 70 | 21.96 | −0.01 | 3.15 | −0.22 | 2.63 | 0.11 |
| 75 | 20.39 | 0.01 | 2.69 | 0.06 | 2.58 | −0.03 |
| 80 | 18.20 | 0.02 | 2.74 | −0.27 | 1.98 | 0.31 |

TABLE 18

| ANGLE | L-EXT | | a-EXT | | b-EXT | |
|---|---|---|---|---|---|---|
| (deg) | GONIO | MODEL-G | GONIO | MODEL-G | GONIO | MODEL-G |
| 10 | 73.69 | −2.09 | 7.88 | 0.25 | 8.48 | 0.08 |
| 15 | 64.30 | −0.59 | 7.28 | 0.00 | 7.56 | 0.05 |
| 20 | 56.28 | 0.16 | 6.56 | −0.05 | 6.64 | 0.10 |
| 25 | 49.27 | 0.57 | 5.88 | −0.05 | 5.85 | 0.09 |
| 30 | 43.47 | 0.46 | 5.30 | −0.09 | 5.22 | 0.01 |
| 35 | 38.60 | 0.21 | 4.82 | −0.12 | 4.60 | 0.01 |
| 40 | 34.62 | −0.12 | 4.37 | −0.09 | 4.21 | −0.13 |
| 45 | 31.33 | −0.35 | 4.09 | −0.15 | 3.80 | −0.14 |
| 50 | 28.61 | −0.43 | 3.84 | −0.17 | 3.50 | −0.18 |
| 55 | 26.42 | −0.43 | 3.56 | −0.09 | 3.22 | −0.16 |
| 60 | 24.62 | −0.36 | 3.49 | −0.17 | 2.97 | −0.13 |
| 65 | 23.08 | −0.25 | 3.31 | −0.14 | 2.78 | −0.11 |
| 70 | 21.60 | −0.11 | 3.03 | 0.00 | 2.42 | 0.09 |
| 75 | 19.93 | 0.04 | 2.89 | −0.05 | 2.35 | −0.02 |
| 80 | 18.01 | −0.16 | 2.54 | 0.01 | 1.66 | 0.42 |

Table 19 below sets forth parameters of the model of the present invention (equation 1) computed from spectrophotometric data for specimen 692, while Table 20 below sets forth the model parameters for specimen 692 as measured and calculated by preferred embodiment flake colorimeter 100.

TABLE 19

| FLAKE | | |
|---|---|---|
| Y = | | 10.60 |
| A = | | 11.15 |
| B = | | 11.83 |
| WIDTH = | | 19.26 deg. |
| | DIFFUSE | |
| Y = | | 4.14 |
| A = | | 13.44 |
| B = | | 12.51 |

TABLE 20

| FLAKE | |
|---|---|
| Y = | 10.60 |
| A = | 14.38 |
| B = | 8.66 |

TABLE 20-continued

| WIDTH = | | 19.40 deg. |
|---|---|---|
| | DIFFUSE | |
| Y = | | 4.23 |
| A = | | 17.30 |
| B = | | 13.16 |

Tables 21 and 22 below correspond to Tables 19 and 20, respectively, except that they contain the model parameters for specimen 693.

TABLE 21

| FLAKE | | |
|---|---|---|
| Y = | | 10.97 |
| A = | | 11.07 |
| B = | | 11.86 |
| WIDTH = | | 18.95 deg. |
| | DIFFUSE | |
| Y = | | 3.99 |
| A = | | 14.17 |
| B = | | 11.66 |

TABLE 22

| FLAKE | | |
|---|---|---|
| Y = | | 10.97 |
| A = | | 14.47 |
| B = | | 8.71 |
| WIDTH = | | 19.16 deg. |
| | DIFFUSE | |
| Y = | | 4.19 |
| A = | | 17.28 |
| B = | | 12.88 |

Tables 23 and 24 below list, respectively, goniometric data for specimen 692 obtained by interpolating the goniospectrophotometric data for the nominal angles of measurement of the preferred embodiment, and the goniometric data measured and calculated for specimen 692 by preferred embodiment flake colorimeter 100.

TABLE 23

| | 18.75 deg. |
|---|---|
| L = | 57.12 |
| a = | 6.55 |
| b = | 6.81 |
| | 38.50 deg. |
| L = | 35.91 |
| a = | 4.51 |
| b = | 4.45 |
| | 73.00 deg. |
| L = | 21.07 |
| a = | 2.83 |
| b = | 2.64 |

TABLE 24

| | 20 deg. |
|---|---|
| L = | 56.94 |
| a = | 8.82 |
| b = | 5.67 |
| | 40 deg. |
| L = | 36.39 |
| a = | 4.97 |
| b = | 3.10 |
| | 75 deg. |
| L = | 21.35 |
| a = | 3.57 |
| b = | 2.62 |

Tables 25 and 26 correspond to Tables 23 and 24, respectively, except that they list the results for specimen 693.

TABLE 25

| | 18.75 deg. |
|---|---|
| L = | 58.18 |
| a = | 6.67 |
| b = | 6.88 |
| | 38.50 deg. |
| L = | 35.74 |
| a = | 4.44 |
| b = | 4.34 |
| | 73.00 deg. |
| L = | 20.63 |
| a = | 2.92 |
| b = | 2.41 |

TABLE 26

| | 20 deg. |
|---|---|
| L = | 58.03 |
| a = | 9.20 |
| b = | 5.69 |
| | 40 deg. |
| L = | 36.46 |
| a = | 4.69 |
| b = | 3.17 |
| | 75 deg. |
| L = | 21.18 |
| a = | 3.55 |
| b = | 2.56 |

By comparing the model parameter results set forth in Tables 20 and 22 above, it can be seen that the main difference between two sets of parameters is a 0.24° difference in the width factor (the results set forth in Tables 19 and 21 demonstrate a 0.31° difference in the width factor). This difference in width factor, as discussed previously, results from different mean flake orientation in the two samples (such as might be caused by different wet vehicle surface tension, different film thicknesses, or different spray-gun pressure, etc.).

E(3) EXAMPLE 3

SPECIMEN 687

The final specimen 687 consisted (as mentioned above) of golden flakes in a transparent layer over a red diffuse sublayer. This specimen places a stringent test on the model of the present invention, and particularly on the assumption that the chromaticity of the flake component is constant with respect to polar angle.

Table 27 below sets forth a comparison of the goniophotometric data for specimen 687 with the data obtained by fitting the modeling function of equation 1 at three angles.

TABLE 27

| ANGLE (deg) | L-EXT | | a-EXT | | b-EXT | |
|---|---|---|---|---|---|---|
| | GONIO | MODEL-G | GONIO | MODEL-G | GONIO | MODEL-G |
| 10 | 91.26 | −6.84 | 5.73 | −1.25 | 36.04 | −2.35 |
| 15 | 69.84 | −1.90 | 9.06 | −1.19 | 27.73 | −0.83 |
| 20 | 55.31 | 0.53 | 12.01 | −0.77 | 21.54 | 0.33 |
| 25 | 45.60 | 1.06 | 15.09 | −0.40 | 17.49 | 0.52 |
| 30 | 39.03 | 0.82 | 17.89 | 0.21 | 14.68 | 0.42 |
| 35 | 34.99 | 0.04 | 20.09 | 1.11 | 13.00 | 0.01 |
| 40 | 32.08 | −0.24 | 22.09 | 1.59 | 11.80 | −0.20 |
| 45 | 30.21 | −0.40 | 23.43 | 1.98 | 11.04 | −0.34 |
| 50 | 29.07 | −0.50 | 24.46 | 2.00 | 10.61 | −0.46 |
| 55 | 28.15 | −0.41 | 25.31 | 1.67 | 10.16 | −0.37 |
| 60 | 27.21 | −0.11 | 26.13 | 0.94 | 9.73 | −0.20 |
| 65 | 26.40 | 0.05 | 26.14 | 0.67 | 9.41 | −0.13 |
| 70 | 25.61 | −0.03 | 25.86 | 0.29 | 9.10 | −0.14 |
| 75 | 24.22 | 0.02 | 25.04 | −0.16 | 8.41 | 0.08 |
| 80 | 22.10 | −0.18 | 22.24 | 0.30 | 7.77 | −0.10 |

Table 28 sets forth the parameters of the model in accordance with the present invention as calculated from goniospectrophotometric data obtained for specimen 687, while Table 29 below sets forth the model parameters as measured and calculated by preferred embodiment flake colorimeter 100 for specimen 687.

TABLE 28

| | FLAKE | |
|---|---|---|
| Y = | | 9.44 |
| A = | | 0.76 |
| B = | | 40.12 |
| WIDTH = | | 14.25 deg. |
| | DIFFUSE | |

TABLE 28-continued

| | |
|---|---|
| Y = | 7.08 |
| A = | 102.48 |
| B = | 35.03 |

TABLE 29

| | FLAKE | |
|---|---|---|
| Y = | | 9.54 |
| A = | | −3.15 |
| B = | | 35.59 |
| WIDTH = | | 13.84 deg. |
| | DIFFUSE | |
| Y = | | 8.43 |
| A = | | 114.49 |
| B = | | 37.29 |

Table 30 below sets forth the goniometric data (L, a, b values) interpolated for the three angles of interest from goniospectrophotometric data measured for specimen 687.

TABLE 30

| | 18.75 deg. |
|---|---|
| L = | 58.45 |
| a = | 11.19 |
| b = | 22.91 |
| | 38.50 deg. |
| L = | 32.84 |
| a = | 21.48 |
| b = | 12.12 |
| | 73.00 deg. |
| L = | 24.85 |
| a = | 25.47 |
| b = | 8.71 |

Table 31 below lists the goniometric values as measured and calculated by preferred embodiment flake colorimeter 100 for specimen 687.

TABLE 31

| | 20 deg. |
|---|---|
| L = | 59.62 |
| a = | 17.18 |
| b = | 21.72 |
| | 40 deg. |
| L = | 34.39 |
| a = | 26.67 |
| b = | 12.25 |
| | 75 deg. |
| L = | 27.07 |
| a = | 30.78 |
| b = | 10.09 |

The agreement on an absolute basis in an extreme case such as specimen 687 between the model parameters (see Table 29) and the physical characteristics of the specimen shows that the model of the present invention is capable of handling such differences very satisfactorily (it is differences which are important when using a flake colorimeter 100 for quality control). The preferred embodiment flake colorimeter 100 provides results which generally follow those of the goniospectrophotometer. However, in order to deal with such extreme specimens most reliably, abridged goniospectrophotometric data (rather than filter colorimeter data) can be used.

While the present invention has been described with what is presently considered to be the most practical and preferred embodiments, it is to be understood that the appended claims are not to be limited to disclosed embodiments, but on the contrary, are intended to cover all modifications, variations and/or equivalent arrangements which retain any of the novel features and advantages of this invention. By way of non-limiting example, model parameters of the present invention could be calculated from measurements performed at more than three angles and, if desired, from a large range of angles (e.g., from the data produced by a spectrophotometer) if desired. Moreover, three viewing angles other than 20°, 40° and 75°, might be used instead. Although the preferred embodiment directs incident light normal to the specimen under measurement, other source angles could be used if desired. It will also be understood that the particular colorimetric measurement techniques of the preferred embodiment could be modified, or entirely different measurement techniques could be substituted, provided sufficient information is available to calculate the parameters of the model of the present invention.

What is claimed is:

1. A method for characterizing a surface painted with a paint of the type having a plurality of nearly flat reflective flakes embedded therein, said method comprising the steps of:
    (1) directing a beam of light toward said surface;
    (2) independently receiving portions of said beam of light reflected and/or scattered by said surface in a plurality of different directions;
    (3) determining the spectral content of the light reflected by said surface in each of said plurality of different directions;
    (4) in response to said determined spectral contents, characterizing the distribution of light reflected by said embedded flakes in directions other than said plurality of directions according to a statistical method describing the orientation of said flakes; and
    (5) producing and outputting electrical signals indicating said characterization.

2. A method as in claim 1 wherein said characterizing step (4) includes characterizing the distribution of light reflected by said flakes in all directions according to said statistical model.

3. A method as in claim 1 wherein said characterizing step (4) includes the step of determining a statistical distribution function describing light reflected by said embedded flakes with respect to polar angle.

4. A method as in claim 3 wherein said distribution function determining step includes calculating a statistical value describing the range of directions over which said embedded flakes are likely to reflect light.

5. A method as in claim 4 wherein said distribution function determining step further includes calculating a further value describing the total amount of light reflected by said embedded flakes.

6. A method as in claim 3 where said distribution function defines a single-dimension normal statistical distribution.

7. An apparatus for characterizing a surface painted with a paint of the type having a plurality of nearly flat reflective flakes embedded therein, said apparatus comprising:
    means for directing a beam of light toward said surface;
    means for independently receiving portions of said beam of light reflected and/or scattered by said surface in a plurality of different directions;

means connected to said receiving means for determining the spectral content of the light reflected by said surface in each of said plurality of different directions;

means connected to said determining means for characterizing, in response to said determined spectral contents, the distribution of light reflected by said embedded flakes in directions other than said plural directions according to a statistical model describing the orientation of said flakes; and means connected to said characterizing means for producing electrical signals indicating said characterization.

8. An apparatus as in claim 7 wherein said characterizing means characterizes the distribution of light reflected by said flakes in all directions according to said statistical model.

9. An apparatus as in claim 7 wherein said characterizing means determines a statistical distribution function describing light reflected by said embedded flakes with respect to polar angle.

10. An apparatus as in claim 9 wherein said characterizing means calculates a statistical value describing the range of directions over which said embedded flakes are likely to reflect light.

11. An apparatus as in claim 10 wherein said characterizing means calculates a further value describing the total amount of light reflected by said embedded flakes.

12. An apparatus as in claim 9 wherein said distribution function defines a single-dimension normal distribution.

13. A measurement apparatus of the type including radiation sensing means for receiving radiation reflected by a finish having flakes embedded therein along first, second and third paths and for converting said received radiation into corresponding first, second and third electrical input signal, and a digital signal processor means connected to receive said electrical input signals and adapted to perform the following functions:

(1) producing, in response to said electrical input signals, a first output signal representing the spectral content of a component of radiation diffusely reflected by said finish;

(2) producing, in response to said electrical input signals, a second output signal representing the spectral content of a component of radiation specularly reflected by said flakes embedded in said finish; and (3) producing, in response to said electrical input signals, a third output signal representing the statistical distribution of the orientation of said flakes with respect to a predetermined orientation.

14. A measurement apparatus as in claim 13, wherein said digital signal processor means is also adapted to perform in the following further functions:

(4) storing first, second and third predetermined signals respectively representing (a) the spectral content of a component of radiation diffusely reflected by a further finish having flakes embedded therein, (b) the spectral content of a component of radiation specularly reflected by the flakes embedded in said further finish, and (c) the statistical distribution of the orientation of said flakes embedded in said further finish with respect to said predetermined orientation;

(5) comparing said first, second and third output signals within stored first, second and third predetermined signals; and (6) producing indicia of the degree of correspondence between the optical characteristics of said first-mentioned finish and said further finish in response to said comparison.

15. An apparatus as in claim 13 wherein:

said radiation sensing means includes colorimetric means for measuring the spectral content of said reflected radiation and for producing said first, second and third input signals in response to said measured spectral contents; and said processor means processes said first and second output signals in response to said measured spectral contents.

16. An apparatus as in claim 13 wherein said processor means produces said third output signal by calculating the value of a statistical width function W in response to said input signals, said width function including:

(a) a first factor representing the statistical distribution of flake orientation in a flake finish wherein embedded flakes are bound to lie substantially parallel to the surface of the finish;

(b) a second factor representing the statistical distribution of flake orientation in a flake finish wherein embedded flakes are free to orient themselves in any position; and (c) an empirical transition factor modifying said first and second factors for the statistical distribution of flake orientation in a flake finish wherein embedded flakes are neither bound to lie substantially parallel to the finish surface nor are free to orient themselves in any position.

17. An apparatus as in claim 16 wherein said width function value is calculated independently of the spectral content of said component of radiation specularly reflected by said flakes.

18. A method of characterizing a finish having flakes embedded therein comprising the steps of:

(1) receiving radiation reflected by said finish along first, second and third paths;

(2) converting said received radiation into first, second and third electrical input signals corresponding to said received radiation reflected along said first, second and third paths, respectively;

(3) producing, in response to said electrical input signals, a first output signal representing the spectral content of a component of radiation diffusely reflected by said finish;

(4) producing, in response to said electrical input signals, a second output signal representing the spectral content of a component of radiation specularly reflected by said flakes embedded in said finish; and (5) producing, in response to said electrical input signals, a third output signal representing the statistical distribution of the orientation of said flakes with respect to a predetermined orientation.

19. A method as in claim 18 further including the steps of (6) storing first, second and third predetermined signals respectively representing (a) the spectral content of a component of radiation diffusely reflected by a further finish having flakes embedded therein, (b) the spectral content of a component of radiation specularly reflected by the flakes embedded in said further finish, and (c) the statistically distribution of the orientation of said flakes embedded in said further finish with respect to said predetermined orientation;

(7) comparing said first, second and third output signals produced by steps (3)–(5) with said stored first, second and third predetermined signals, and (8) producing indicia of the degree of correspondence between the characteristics of said first-mentioned finish and said further finish in response to said comparison.

20. A method as in claim 18 wherein:

said converting step (2) comprises the step of producing said first, second and third input signals in response to the spectral content of the reflected radiation received by said receiving step (1); and said producing steps (3) and (4) produces said first and second output signals, respectively, each in response to said spectral content.

21. A method as in claim 18 wherein said producing step (5) includes the step of calculating the value of a statistical width function W in response to said input signals, said width function calculating step including the steps of:

(a) calculating the value of a first factor representing the statistical distribution of flake orientation in a flake finish wherein embedded flakes are bound to lie substantially parallel to the surface of the finish in response to said input signals;

(b) calculating the value of a second factor representing the statistical distribution of flake orientation in a flake finish wherein embedded flakes are free to orient themselves in any position in response to said input signals;

(c) calculating the value of an empirical transition factor representing the statistical distribution of flake orientation in a flake finish wherein embedded flakes are neither bound to lie substantially parallel to the finish surface nor are free to orient themselves in any position in response to said input signals; and (d) modifying the values calculated by said calculating steps (a) and (b) with the value calculated by said calculating step (c).

22. A method as in claim 21 wherein said calculating steps (a), (b) and (c) calculate said first, second and transition factors, respectively, independently of the spectral content of said component of radiation specularly reflected by said flakes.

23. A method of characterizing a finish having flakes embedded therein comprising the steps of:

(1) receiving radiation reflected by said finish along first, second and third paths;

(2) converting said received radiation into first, second and third sets of electrical input signals corresponding to the spectral content of said radiation reflected along said first, second and third paths;

(3) calculating colorimetric coordinates for each of said first path, second path and third path radiation in response to said electric input signals;

(4) determining the value of a width parameter W in response to said colorimetric coordinates, said width parameter representing the expected range over which a component of radiation specularly reflected by said flakes embedded in said finish is reasonably large;

(5) calculating a flake component weighted mean reflectance factor FBAR in response to said width parameter W;

(6) defining a statistical flake distribution function in response to said width parameter W;

(7) evaluating said statistical flake distribution function for each of said first, second and third paths;

(8) generating a set of weighted mean colorimetric parameters for said specularly-reflected component of radiation in response to said calculated factor FBAR, said colorimetric coordinates and the results of said evaluating step (7);

(9) generating a set of weighted mean colorimetric parameters for a component of radiation diffusely reflected by said finish in response to said calculated value FBAR, said colorimetric coordinates and the results of said evaluating step (7); and

(10) displaying said width parameter W and said sets of parameters generated by said generating steps (8) and (9).

24. A method as in claim 23 further including the steps of:

(11) comparing said parameters displayed by said displaying step with predetermined similar parameters corresponding to a standard finish; and

(12) varying properties of a mixture applied by a mixture-applying apparatus in response to said comparison.

25. A method as in claim 23 wherein said function defined by said function-defining step (6) has the form $$F(\theta') = \frac{\cos(\theta'/2) * e^{ln(\frac{1}{2})*(\theta'/W)^2}}{(FTRAN(W) * \sin(\theta')) + 1 - FTRAN(W)}$$

where $$FTRAN(W) = \frac{1}{(1 + e^{(W-T1)/T2})}$$

$T_1$ and $T_2$ are predetermined constants, and $\theta'$ is a variable; and said evaluating step (7) includes the step of successively setting said variable $\theta'$ to values corresponding to the polar angles within said finish of radiation travelling along said first, second and third paths after exiting said finish.

26. A method as in claim 23 wherein:

said method further includes the step of directing a radiation beam normal to the surface of said finish; and said receiving step (1) comprises the step of receiving radiation reflected by said finish along a first path about 20° from said surface normal, along a second path about 40° from said surface normal, and along a third path about 75° from said surface normal.

27. A method as in claim 23 wherein said determining step (4) includes the steps of:

(1) averaging said colorimetric coordinates for said first, second and third path radiation; and (2) computing a single width parameter W in response to the resulting average.

28. A measurement apparatus of the type including radiation sensing means for receiving radiation reflected by a finish having flakes embedded therein, a converting means coupled to said measuring means for converting said received radiation into first, second and third electrical input signals respectively representing the colorimetric coordinates of radiation reflected by said finish along first, second and third distinct paths, and a digital signal processor means connected to receive said electrical input signals and adapted to perform the following functions:
  (1) determining, in response to said electrical input signals, the value of a width parameter W in response to said colorimetric coordinates, said width parameter representing the expected range over which a component of radiation specularly reflected by said flakes is reasonably large;
  (2) calculating a flake component weighted mean reflectance factor FBAR in response to said width parameter W;
  (3) defining a statistical flake distribution function in response to said width parameter W;
  (4) evaluating said statistical flake distribution function for each of said first, second and third paths;
  (5) generating a set of weighted mean colorimetric parameters for said specularly-reflected component in response to said calculated factor FBAR, said colorimetric coordinates, and the results of said statistical flake distribution function evaluation;
  (6) generating a set of weighted mean colorimetric parameters for a component of radiation diffusely reflected by said finish in response to said calculated factor FBAR, said colorimetric coordinates, and the results of said statistical flake distribution function evaluation; and
  (7) producing electrical output signals responsive to said width parameter W and to said generated sets of weighted mean colorimetric parameters corresponding to said diffusely-reflected and flake components of radiation.

29. A measuring apparatus as in claim 28 wherein said processing means is adapted to perform the following further functions:
  (8) comparing said electrical output signals with predetermined stored similar signals corresponding to a standard finish; and
  (9) varying the properties of a mixture applied by a mixture-applying apparatus in response to said comparison.

30. A measuring apparatus as in claim 28 wherein said statistical flake distribution function has of the form $$F(\theta') = \frac{\cos(\theta'/2) * e^{ln(\frac{1}{2})*(\theta'/W)^2}}{(FTRAN(W) * \sin(\theta')) + 1 - FTRAN(W)}$$

where $$FTRAN(W) = \frac{1}{(1 + e^{(W-T1)/T2})}$$

$T_1$ and $T_2$ are predetermined constants, and $\theta'$ is a variable; and
  said processor means evaluates said function by successively setting said variable $\theta'$ to values corresponding to polar angles within said finish of radiation travelling along said first, second and third paths after exiting said finish.

31. A measuring apparatus as in claim 28 wherein:
  said apparatus further includes means for directing a radiation beam normal to the surface of said finish; and
  said radiation sensing means comprises means for receiving radiation reflected by said finish along a first path about 20° from said surface normal, along a second path about 40° from said surface normal, and along a third path about 75° from said surface normal.

32. A measuring apparatus as in claim 28 wherein said processor means is adapted to form the following subfunctions of said determining function (1):
  (a) averaging said colorimetric coordinates for said first, second and third path radiation; and
  (b) computing a single width parameter W in response to said resulting average.

* * * * *